(12) United States Patent
Kibar et al.

(10) Patent No.: US 8,698,031 B2
(45) Date of Patent: *Apr. 15, 2014

(54) SEPARATION AND MANIPULATION OF A CHIRAL OBJECT

(75) Inventors: Osman Kibar, San Diego, CA (US); Mirianas Chachisvilis, La Jolla, CA (US); Eugene Tu, San Diego, CA (US); Thomas H. Marsilje, San Diego, CA (US)

(73) Assignee: Dynamic Connections, LLC, San Diego, CA (US)

( * ) Notice: Subject to any disclaimer, the term of this patent is extended or adjusted under 35 U.S.C. 154(b) by 930 days.

This patent is subject to a terminal disclaimer.

(21) Appl. No.: 12/142,545

(22) Filed: Jun. 19, 2008

(65) Prior Publication Data
US 2008/0274555 A1    Nov. 6, 2008

Related U.S. Application Data

(63) Continuation-in-part of application No. 12/103,281, filed on Apr. 15, 2008, now Pat. No. 7,935,906.

(60) Provisional application No. 60/912,309, filed on Apr. 17, 2007, provisional application No. 60/987,674, filed on Nov. 13, 2007.

(51) Int. Cl.
| | | |
|---|---|---|
| *B03C 7/00* | (2006.01) | |
| *G01N 1/18* | (2006.01) | |
| *C07B 57/00* | (2006.01) | |
| *B03C 7/02* | (2006.01) | |
| *B03C 1/24* | (2006.01) | |

(52) U.S. Cl.
CPC ............. *C07B 57/00* (2013.01); *B03C 7/026* (2013.01); *B03C 1/24* (2013.01)

USPC ......... 209/127.1; 209/212; 422/68.1; 436/71; 436/86; 436/94; 436/177; 435/173.1; 435/243; 435/252.1; 435/235.1

(58) Field of Classification Search
CPC ............ B03C 1/24; B03C 7/026; C07B 57/00
See application file for complete search history.

(56) References Cited

U.S. PATENT DOCUMENTS 5,578,212 A * 11/1996 Pirkle et al. ................... 210/638
5,752,606 A    5/1998 Wilson et al.

(Continued)

FOREIGN PATENT DOCUMENTS

| CN | 101687155 A | 3/2010 |
|---|---|---|
| CN | 102016021 | 4/2011 |

(Continued)

OTHER PUBLICATIONS

PCT application No. PCT/US2008/60444, filed on Apr. 16, 2008, including application as filed.

(Continued)

*Primary Examiner* — Dirk Bass
(74) *Attorney, Agent, or Firm* — Fish & Richardson P.C.

(57) ABSTRACT

Among other things, for use in directional motion of chiral objects in a mixture, a field is applied across the chamber and is rotating relative to the chamber to cause rotation of the chiral objects. The rotation of the objects causes them to move directionally based on their chirality. The method applies to sugars, proteins, and peptides, among other things, and can be used in a wide variety of applications.

21 Claims, 17 Drawing Sheets

(56) References Cited

U.S. PATENT DOCUMENTS

| | | | |
|---|---|---|---|
| 6,288,206 | B1 | 9/2001 | Stewart et al. |
| 6,344,121 | B1 | 2/2002 | Stalcup et al. |
| 7,935,906 | B2 | 5/2011 | Kibar et al. |
| 2004/0241718 | A1 | 12/2004 | McGown |
| 2005/0094144 | A1 | 5/2005 | Gibbs et al. |
| 2005/0118570 | A1* | 6/2005 | Hollis et al. ............ 435/5 |
| 2006/0073540 | A1 | 4/2006 | Martel |
| 2006/0289341 | A1 | 12/2006 | Muller et al. |
| 2008/0262240 | A1 | 10/2008 | Kibar et al. |
| 2008/0274555 | A1 | 11/2008 | Kibar et al. |
| 2008/0296157 | A1 | 12/2008 | Bauer et al. |
| 2009/0239281 | A1 | 9/2009 | Kibar et al. |
| 2011/0132812 | A1 | 6/2011 | Kibar et al. |

FOREIGN PATENT DOCUMENTS

| | | |
|---|---|---|
| CN | ZL200880020591.1 | 1/2013 |
| EP | 2134697 | 12/2009 |
| EP | 2265714 | 12/2010 |
| EP | 2304425 | 4/2011 |
| JP | 2010-527284 | 8/2010 |
| WO | WO94/16821 | 8/1994 |
| WO | WO2007/039209 | 4/2007 |
| WO | WO2007/146675 | 12/2007 |
| WO | WO2008/130980 | 10/2008 |
| WO | WO2009/117573 | 9/2009 |
| WO | WO2009/155406 | 12/2009 |

OTHER PUBLICATIONS

Baranova et al., "Separation of Mirror Isomeric Molecules by Radio-Frequency Electric Field of Rotating Polarization", Chemical Physics Letters, vol. 57, No. 3, Aug. 1, 1978, pp. 435-437.
Evans et al., "The Effect of External Electric Fields on Molecular Liquids and Induced Translational Motion", Journal of Molecular Liquids, 29, 1984, pp. 11-35.
Gel'Mukhanov et al., "Orientation of Stereoisomers by Electromagnetic Field", Optics Communications, vol. 53. No. 6, Apr. 15, 1985, pp. 381-384.
Purcell, "The Efficiency of Propulsion by a Rotating Flagellum", Proceedings of the National Academy of Sciences, vol. 94, pp. 11307-11311, Oct. 1997.
U.S. Appl. No. 60/912,309, filed Apr. 17, 2007, including application as filed.
U.S. Appl. No. 60/987,674, filed Nov. 13, 2007, including application as filed.
U.S. Appl. No. 12/103,281, filed Apr. 15, 2008, including application as filed (including pending claims).
Chankvetadze, B., "Enantioseparation of Chiral Drugs and Current Status of Electromigration Techniques in This Field", Journal of Separation Sciences, 2001, vol. 24, Issue 9, pp. 691-705, Oct. 25, 2001.
Nakata, M., et al., "Electric-Field-Induced Chirality Flipping in Smectic Liquid Crystals: The Role of Anisotropic Viscosity", Physical Review Letters, vol. 96, 067802, pp. 1-4, 2006, Feb. 16, 2006.
Forster et al., "Use of Moving Optical Gradient for Analysis of Apoptotic Cellular Responses in a Chronic Myeloid Leukemia Cell Model", Anal. Biochem., Apr. 2004 1:327 (1):14-22, entire document, particularly pp. 1-5.
Paredes, et al., Stimulated Moving Bed Chromatography from chiral molecules to biocompounds. Analytica World, 2004.
PCT application No. PCT/US2008/60444 filed on Apr. 16, 2008, including application as filed.
International Search Report and Written Opinion mailed Nov. 7, 2008, in corresponding PCT application No. PCT/US2008/60444 (42 pages).
U.S. Appl. No. 61/038,573, filed Mar. 21, 2008, including application as filed.
U.S. Appl. No. 12/407,380, filed Mar. 19, 2009, including application as filed (including pending claims).
PCT application No. PCT/US2009/037661 filed on Mar. 19, 2009, including application as filed.
International Search Report and Written Opinion mailed Jul. 21, 2009, in corresponding PCT application No. PCT/US2009/037661 (24 pages).
PCT application No. PCT/US2009/047778 filed on Jun. 18, 2009, including application as filed.
International Search Report and Written Opinion mailed Aug. 11, 2009, in corresponding PCT application No. PCT/US2009/047778 (8 pages).
International Preliminary Report on Patentability mailed Oct. 29, 2009 in PCT application No. PCT/US2008/060444 (18 pages).
USPTO Non Final Office Action in U.S. Appl. No. 12/407,380, dated Dec. 23, 2011, 8 pages.
Chinese Office Action with English translation from Chinese Application No. 200880020591.1 issued Jan. 6, 2012 (11 pages).
Chinese Office Action with English translation from Chinese Application No. 200980113998.3 issued Jan. 31, 2012 (4 pages).
European Communication from European Application No. 08745951.7 dated May 20, 2010 (2 pages).
U.S. Appl. No. 13/028,448, filed Mar. 7, 2012.
Transaction history and pending claims of U.S. Appl. No. 12/407,380, filed Mar. 7, 2012.
International Preliminary Report on Patentability mailed Jan. 6, 2011, in corresponding PCT application No. PCT/US2009/047778 (7 pages).
Office Action from Russian Patent application No. RU2009142226 mailed Mar. 31, 2010 (6 pages).
U.S. Appl. No. 13/028,448, filed Feb. 16, 2011, including application as filed (including pending claims).
Transaction history of U.S. Appl. No. 13/028,448, filed May 9, 2011.
Transaction history of U.S. Appl. No. 12/407,380, filed May 9, 2011.
Transaction history of U.S. Appl. No. 12/103,281, filed May 9, 2011.
U.S. Appl. No. 13/028,448, filed Jun. 14, 2011.
U.S. Appl. No. 12/407,380, filed Jun. 14, 2011.
USPTO Non Final Office Action in U.S. Appl. No. 12/103,281, dated Jun. 16, 2010, 22 pages.
International Preliminary Report on Patentability mailed Sep. 30, 2010, in corresponding PCT application No. PCT/US2009/037661 (8 pages).
European communication from EP Application No. 09767715.7 issued Feb. 1, 2011 (2 pages).
European Search Report from EP Application No. 09767715.7 issued Jan. 16, 2012 (89 pages).
European communication from EP Application No. 09767715.7 issued Jan. 27, 2012 (6 pages).
Response to Chinese Office Action with English translation from Chinese Application No. 200880020591.1 issued Jan. 6, 2012, filed Mar. 21, 2012 (46 pages).
Chinese Office Action with English translation from Chinese Application No. 200880020591.1 issued May 30, 2012 (7 pages).
Response to Chinese Office Action from Chinese Application No. 200980113998.3 issued Jan. 31, 2012, filed Jun. 14, 2012 (4 pages).
Response to Chinese Office Action with English translation from Chinese Application No. 200880020591.1 issued May 30, 2012, filed Aug. 14, 2012 (24 pages).
USPTO Non Final Office Action in U.S. Appl. No. 13/028,448, dated Aug. 1, 2012 (6 pages).
U.S. Sppl. No. 13/028,448, filed Sep. 25, 2012.
Transaction history of U.S. Appl. No. 12/407,380, filed Sep. 25, 2012.
European Communication from European Application No. 09721269.0 dated Oct. 6, 2011 (6 pages).
Kirkinis, E., et al., "Electromagnetic propulsion and separation by chirality of nanoparticles in liquids", arXiv:1104.0026v1 [cond-mat.soft], University of Washington, Department of Applied Mathematics and Physics, Seattle, Washington, Mar. 31, 2011. (4 pages).
U.S. Appl. No. 13/028,448, filed Oct. 7, 2011.
U.S. Appl. No. 12/407,380, filed Oct. 7, 2011.
Chinese Office Action from Chinese Application No. 200880020591.1 issued Sep. 15, 2011 (3 pages).

(56) References Cited

OTHER PUBLICATIONS

Response to office action issued Sep. 15, 2011 in Chinese Application No. 200880020591.1, filed Nov. 9, 2011 (21 pages).
U.S. Appl. No. 13/028,448, filed Dec. 6, 2011.
U.S. Appl. No. 12/407,380, filed Dec. 6, 2011.
Chinese Office Action in English translation form from Chinese Application No. 200980113998.3 issued Nov. 2, 2012 (4 pages).
Response to Chinese Office Action from Chinese Application No. 200980113998.3 issued Nov. 2, 2012, filed Jan. 17, 2013 (17 pages).
Response to European Communication from European Application No. 09721269.0 dated Oct. 6, 2011, filed Mar. 30, 2012 (12 pages).
U.S. Appl. No. 13/028,448.
Transaction history of U.S. Appl. No. 12/407,380 as of Mar. 19, 2013.
Chinese Office Action in English translation form from Chinese Application No. 200980113998.3 issued May 27, 2013 (5 pages).

* cited by examiner

| Time | $N_0$ (V) | $N_1$ (V) | $N_2$ (V) | $N_3$ (V) | $N_4$ (V) ... |
|---|---|---|---|---|---|
| $t_1$ | 10 | | | | |
| $t_2$ | 10 | 5 | | | |
| $t_3$ | 10 | 10 | | | |
| $t_4$ | 10 | 5 | 5 | | |
| $t_5$ | 10 | 10 | 5 | | |
| $t_6$ | 10 | 5 | 10 | | |
| $t_7$ | 10 | 10 | 5 | 5 | |
| $t_8$ | 10 | 5 | 10 | 5 | |
| $t_9$ | 10 | 10 | 5 | 10 | |
| $t_{10}$ | 10 | 5 | 10 | 5 | 5 |
| $t_{11}$ | 10 | 10 | 5 | 10 | 5 |
| $t_{12}$ | 10 | 5 | 10 | 5 | 10 |
| $t_{13}$ | ... | | | | |

Total volume of each chamber = 10 (arbitrary units)

FIG. 5

DISCRETE ELECTRODES

SIDE VIEW

SEPARATION AND MANIPULATION OF A CHIRAL OBJECT

This application is a continuation-in-part of U.S. application Ser. No. 12/103,281, filed Apr. 15, 2008, which claims the benefit of priority of U.S. provisional application 60/912,309, filed Apr. 17, 2007, and U.S. provisional application 60/987,674, filed Nov. 13, 2007, and the entire contents of the applications are incorporated here by reference.

BACKGROUND

This description relates to separation and manipulation of a chiral object.

We use the term chiral object (or system) very broadly to include, for example, any object or system that differs from its mirror image such that its mirror image cannot be superimposed on the original object. One kind of chiral object is a chiral molecule, also called an enantiomer. A common feature of chiral molecules is their "handedness" (i.e., right-handed or left-handed). Enantiomers are a subset of chiral objects called stereoisomers. A stereoisomer is one of a set of isomeric molecules whose atoms have similar connectivity but differ in the way the atoms are arranged in space. A stereoisomer includes at least one stereocenter, which is any atom that bears groups such that an interchanging of any two groups leads to a stereoisomer. A stereoisomer may have one or more stereocenters. For example, for a molecule with 3 stereocenters (e.g. S, S, S), its enantiomer would be (R, R, R); epimers are stereoisomers that differ in only one but not all stereocenters (e.g., S, S, R instead of S, S, S). It is also possible for a molecule to be chiral without having a stereocenter (the most common form of chirality in organic compounds). In axial chirality, for example, a molecule does not have a stereocenter but has an axis of chirality, i.e., an axis about which a set of substituents is held in a spatial arrangement that cannot be superimposed on its mirror image. An example is the molecule 1,1'-bi-2-naphthol (BINOL). Although the discussion here refers to enantiomers, it also applies to other stereoisomers, even if they do not qualify as enantiomers. We use the term stereoisomers broadly.

A mixture of molecules is often called racemic if it contains equal amounts of right-handed and left-handed enantiomers, and it is called enantiopure (or, optically pure) if only one type of enantiomer dominates in the mixture. Here, however, we refer to a racemic mixture more broadly to include any non-pure mixture of stereoisomers that is not enantiopure, whether or not the amounts of the stereoisomers are equal.

Chirality is important in chemistry, especially for biological and drug applications. Natural biomolecules are typically found in only one enantiomer form (e.g., proteins, peptides, and amino acids are left-handed, and sugars are right-handed). The fields of drug discovery, development, and manufacturing are interested in molecules that are enantiopure, because one form or enantiomer may work better in vivo while the opposite form may be toxic or may cause side effects. Other chemistry-based fields would also benefit from enantiopure molecules including (for illustration purposes), but not limited to: flavors and fragrances, agrichemicals, fine chemicals, petrochemicals, and others.

Enantiopure samples are sometimes produced by asymmetric synthesis, in which only one form of enantiomer is chemically synthesized from the beginning. Another approach is to synthesize both enantiomers (for example, in a racemic mixture) and then separate the desired enantiomer from the mixture, for example, using column chromatography, in which the mixture is run through a chiral selector (e.g., a chemical matrix that binds preferentially to one enantiomer and less so to its counterpart) iteratively until a desired purity is reached.

Some molecular separation techniques are not effective for chiral molecules, because two counterpart enantiomers generally share physical properties, including chemical composition, charge, size, electric and magnetic dipole moments, and energy levels. Detection and separation of chiral molecules is typically done by interacting the molecules with a chiral medium (e.g., a chemical matrix). Enantiomers also can be identified by their interaction with a chiral (e.g., circularly polarized) electromagnetic field.

SUMMARY

In general, in an aspect, for use in directional motion of chiral objects in a mixture, a field is applied across the chamber and is rotating relative to the chamber to cause rotation of the chiral objects. The rotation of the objects causes them to move directionally based on their chirality.

Implementations may include one or more of the following features. The chiral objects comprise sugar molecules. The sugar molecules comprise at least one of monosaccharides, disaccharides, oligosaccharides, or polysaccharides (glycans). The chiral objects comprise proteins. The chiral objects comprise peptides. A purity of at least one of two enantiomers in a mixture is enhanced by separating molecules of the two enantiomers in each of a series of chambers, the purity of the enantiomer in at least some of the successive chambers being at increasingly higher levels. A portion of at least one of the separated enantiomers is transferred from each of the chambers to a previous one or a next one of the chambers in the series. A result of the directional motion or enhanced purity is used in one or more of the following: genomics, proteomics, glycomics, chemical manufacturing, food processing, forensics, academic research, solvent purification, asymmetric synthesis. A product outcome of a chemical reaction is purified or quantified, or identified. A product outcome of a chemical reaction comprises a non-racemic product mixture or a racemic product mixture.

In general, in an aspect, a chamber holds a mixture containing one or more enantiomers. A field source imposes a rotating field on the mixture. The chamber has an inlet to receive the mixture, and an outlet to remove a portion of the mixture that contains at least one of the enantiomers in an elevated concentration relative to its average concentration in the mixture in the chamber. A chemical reaction vessel is connected to the chamber to hold fluid to be delivered to the chamber. The chamber is used to analyze or process a reaction component in the fluid using the chamber.

Implementations may include one or more of the following features. The analyzing or processing comprises analyzing purity of a reaction component, purification of a reaction component, or determining the absolute configuration of a reaction component. The chiral objects comprise achiral molecules, such as lipids, that have chiral labels attached.

Implementations also may include one or more of the following features. The field delivers insufficient energy to damage the chiral objects. The frequency of rotation causes directional motion at a speed that is high enough to achieve a predetermined degree of separation of some of the chiral objects from the mixture at a predetermined concentration in no more than a predetermined amount of time. The field strength and the speed of rotation of the field are selected to achieve a predetermined level of efficiency of the directional motion. The electric field strength is lower than $10^5$ V/m. The electric field has a rotational frequency higher than 100 M rotations per second. The directional motion has a velocity of at least 0.1 angstrom per revolution (i.e., a millimeter per second at 100 million revolutions per second).

The chiral objects include chiral molecules. The molecules include stereoisomers. The stereoisomers include enantiomers. The stereoisomers include epimers. The chiral objects include aggregates of chiral or achiral molecules or both. The chiral objects include molecules having axial chirality.

The molecules include drug molecules. The molecules include drug intermediate molecules. The stereoisomers have more than one stereocenter. The chiral objects are of one type. The chiral objects are of two types. The chiral objects are of more than two types.

The chirality of the chiral objects is analyzed based on the directional motion. The presence or absence of chiral objects is detected based on the directional motion. Two or more types of chiral objects are separated based on the directional motion. The chiral objects are separated into two groups. The chiral objects are separated into more than two groups. The chiral objects of the two or more types move in opposite directions. The chiral objects of the two or more types move in the same direction but at different average velocities. The chiral objects of the two or more types are separated in real-time. The chiral objects are separated as end-point. The field includes an electric field. The field includes a magnetic field. The field is rotated relative to the chamber in discrete steps. The field is rotated continuously relative to the chamber. The field is rotated around a stationary chamber. The chamber is rotated relative to a field of fixed orientation. The mixture includes a racemic mixture. The field is rotated relative to the chamber in successive angular positions around a central portion of the chamber. The field is applied from electrodes arranged on a peripheral wall of the chamber. The electric field is applied at successive angular orientations across the chamber at intervals that cause the electric field to rotate around the chamber with a selected rotational frequency profile. The rotational frequency profile is in at least one of the ranges of less than 1 kHz, 1 kHz to 10 kHz, 10 kHz to 100 kHz, 100 kHz to 1 MHz, 1 MHz to 10 MHz, 10 MHz to 100 MHz, 100 MHz to 1 GHz, 1 GHz to 10 GHz, or above 10 GHz. The rotational frequency is in the RF range. The rotational frequency is in the microwave range. The field is applied by an electromagnetic beam that is collinear with an axis of the chamber. The electromagnetic beam is circularly polarized. The rotational frequency is in the RF range. The rotational frequency is in the microwave range.

The chiral objects are loaded into the chamber at a particular point along the chamber. The chiral objects are loaded into the chamber without regard to their entry point along the chamber. The field is applied to cause a concentration of the chiral objects to reach a steady state. The field is applied and then turned off before the concentration of the chiral objects reaches a steady state.

The gradient of a concentration of the chiral objects in the mixture in the chamber includes an exponential profile. The gradient includes a linear profile. The gradient includes a nonlinear profile. The parameters associated with the directional motion are non-constant in the direction of the motion.

A chiral label is associated with the chiral objects. Entities are attached to the chiral objects to increase dipole moments of the chiral objects. Entities are attached to the chiral objects to increase a rotational/translational coupling factor.

At least some of the chiral objects are caused to move collectively.

The mixture includes a fluid in which the chiral objects move. The fluid includes a gas. The fluid includes a polar solution. The fluid includes a non-polar solution. The fluid includes a high pressure fluid. The fluid is in a supercritical phase. The fluid's composition or properties are controlled.

The chiral objects exhibit a smaller dipole moment than molecules of the polar solution. The directional motion is achieved by rotating molecules of the fluid to impart angular momentum on the objects to cause them to rotate. The directional motion occurs within a flow of the mixture (e.g., along the chamber). The mixture is caused to flow in a manner that counters the directional motion of the chiral objects. The applied field has a profile other than constant along a direction of the chamber. The direction is orthogonal to a length of the chamber.

The directional motion is controlled using feedback. An outcome of the directional motion is monitored.

The enhancing occurs during processing periods and the transferring occurs in intervals that are at least partly non-overlapping with the processing periods. The portion of the separated enantiomer in each chamber that is transferred is a higher concentration portion or a lower concentration portion than the average concentration in the chamber. The average concentration of each of the enantiomers in each of the chambers remains essentially unchanged over time. There is more than one such series of chambers operated in parallel. The purities of both of the enantiomers are enhanced. The chambers are of the same size. The enantiomers are in a mixture and the mixture is transferred from chamber to chamber. The enantiomers are in a mixture and the enantiomers are extracted from the mixture before being transferred from chamber to chamber. The portion that is transferred is one-quarter. The portion that is transferred is less than one-quarter. The portion that is transferred to the next chamber is different from the portion transferred to the previous chamber. The additional series of chambers have different lengths from the primary series. The output of the additional series of chambers is transferred to the first or last chamber of the primary series. Initial purity levels of the enantiomers are established in each of the chambers. The process is run continuously for real-time purification of one or both enantiomers. The portions of the chiral objects are transferred to and from the chamber using a pump. The pump is mechanical. The pump is not mechanical.

An outcome is monitored chemically. An outcome is monitored optically. An outcome is monitored electronically. Software is used to control, manage, or compliment an outcome. The software calculates or predicts expected performance or performance limits. The software calculates or predicts an average velocity of the chiral objects. The software calculates or predicts a direction of motion of one or more of the chiral objects. The system is fully automated. The system is modular.

Environmental parameters are controlled or optimized, including temperature or pressure. One of the environmental parameters is controlled remotely. Control parameters are optimized, calibrated, or monitored. The control parameter includes applied voltage, rotation frequency, duration of the applied field, or selection of a fluid medium. Performance parameters are also optimized or monitored. The performance parameter includes reliability, repeatability, or reproducibility.

Multiple runs are performed in parallel. Performance runs are allowed or managed in series. The environment for the chiral objects is isotropic. The environment for the chiral objects is anisotropic or asymmetric in at least one dimension of the chamber. Diffusion inside the chamber is reduced. Convection inside the chamber is reduced.

The chamber holds one enantiomer. The chamber holds two enantiomers. The chamber holds more than two enantiomers. A diameter of the chamber is in the millimeter scale. A diameter of the chamber is in the micrometer scale. A diameter of the chamber is in the nanometer scale. The chamber has a cross-section that is circular. The chamber has a cross-section that is non-circular. The electrodes are on an inner wall of the chamber to be in contact with the mixture. The electrodes are on an inner wall of the chamber and not arranged to be in contact with the mixture. The electrodes are on an outer wall of the chamber, but not in contact with the mixture. The electrodes include metal or a semiconductor. The electrodes have a cross-section that is circular. The electrodes have a cross-section that is non-circular. The electrodes have a cross-section that is asymmetric. There are two electrodes. There are three electrodes. There are more than three electrodes. The electric field is applied to only two of the electrodes at a time. The electric field is applied to more than two of the electrodes at a time.

The chamber includes or is part of a disposable. The disposable includes a cartridge. The cartridge includes a chamber to hold a sample. The cartridge includes multiple chambers to hold a sample. The chamber cross-section is circular. The chamber cross-section is non-circular. The chamber includes a capillary. The capillary includes glass. The capillary includes quartz. The capillary includes polymer. The capillary includes material that is not glass, quartz or polymer. The capillary is coated on the inside surface. The chamber includes a microfluidic channel on a chip. The channel is formed by photolithography. The channel is formed by laminating layers of a material. The channel is formed by both photolithography and laminating layers of a material.

The cartridge includes electrodes arranged about the chamber to produce a rotating electric field. The electrodes are placed about the chamber in an axial geometry. The electrodes are placed about the chamber in an orthogonal geometry. The electrodes are placed about the sample chamber at an angle that is not axial or orthogonal. The electrode includes a coil. The electrodes include a continuous set of electrodes per sample chamber. The electrodes include discrete sets of electrodes per sample chamber. The electrodes include a waveguide for circularly polarizing microwave field. The electrodes generate a rotating field with an axis of rotation orthogonal to direction of flow. The rotating field is generated at a T-junction and/or a Y-junction.

The cartridge includes one or more ports to inject and/or extract the sample. The ports include fluidic interconnects. The interconnects include luer fittings. The interconnects include screw fittings. The cartridge includes a detection zone to monitor the concentration of a sample. The cartridge includes a controller to control and/or monitor environmental parameters. The environmental parameter includes pressure. The environmental parameter includes temperature. The cartridge includes a connector to make electrical contact with the electrodes. The connector include electrical interconnects. The capillary is surrounded by electrodes that generate a rotating field whose axis is co-linear with the length of the capillary. The capillary and electrodes are held by a larger tubing. The tubing includes metal. The tubing includes dielectric material.

The electrodes and/or the electrical connections are integrated onto a board. The board includes a printed circuit board. The board includes a through hole for a capillary. The cartridge includes a microfluidic device. The device includes glass. The device includes quartz. The device includes polymer. The polymer includes epoxy. The device includes elastomer.

The electrodes are deposited on or near vertices of the channel. The electrodes are arranged to be in contact with a medium in the sample chamber. The electrodes are arranged to be insulated from a medium in the sample chamber. The channel cross-section is a square. The sample chamber includes a channel. The sample chamber includes multiple channels. The sample chamber includes one or more T- or Y-junctions. The chamber contains a chemical matrix. The matrix includes glass. The matrix includes silica. The matrix includes diatomaceous earth. The matrix includes polymer. A direction of the chiral object's motion is monitored to determine its absolute configuration.

The mixture is non-pure. The mixture is enantiopure. The chiral objects have only one stereocenter. The chiral objects have more than one stereocenter. The direction of the field is reversed for the same chiral objects to confirm the absolute configuration. Software is used to calculate or predict the speed or direction of motion for a chiral object. The apparatus is used as a stand-alone system. The apparatus is used as an add-on to another chiral separation instrument. The field is applied to a chiral HPLC column. The apparatus is used as an add-on to a standard HPLC column. A result is used in analytical chemistry. A result is used in drug discovery. A result is used in drug development. A result is used in drug manufacture. A result is used in medical diagnostics. A result is used in fine chemical or synthetic intermediate manufacture. A result is used in agrochemicals. A result is used in petrochemicals. A result is used in flavors and fragrances. A result is used in process monitoring.

The chiral objects include achiral objects with chiral labels attached. The chiral objects include unknown molecules. The chiral objects include known molecules.

A result is used to quantify a specific property of the chiral object. The specific property of the chiral object includes its propeller propulsion efficiency. The specific property of the chiral object includes its absolute configuration. The specific property of the chiral object includes its presence or absence in the solution. The specific property of the chiral object includes the magnitude or the orientation of its dipole moment. The system or the resulting separations are using in electro-rotary chemistry. The electro-rotary chemistry includes chiral synthesis. The electro-rotary chemistry includes reactions or applications involving catalysis. The electro-rotary chemistry includes the study or the detection of molecular interactions. The spatial concentration profile of the chiral molecules is changed to manipulate the chemical reactions involving them. The system is used to separate or purify the chiral molecules from achiral impurities in the solution. The chiral labels are self-assembled. The chiral labels are self-activated. The chiral labels are pre-activated. The achiral objects include molecules, such as DNA, RNA, peptides, proteins or amino acids. The achiral objects include living organisms, such as viruses, bacteria or cells. More than one type of chiral label is used for multiplex assays. The chiral labels are used for debulking or enriching sample matrices.

The chiral labels comprise propeller entities. The propeller entities are conjugated to antibodies or nucleic acids. The propeller entities comprise at least two components. The chiral labels comprise aptamers. The aptamers become chiral or reverse their chirality upon binding to achiral objects. Intermolecular interactions are induced to convert achiral objects into chiral objects. Intermolecular interactions are induced to change the propeller efficiency of chiral objects.

The technique enables stereoseparation of previously unseparated racemic drugs, such as metaxalone. Accordingly another aspect of the invention features compositions that are enantomerically enriched in + metaxalone or in − metaxalone. Enantiomerically enriched means that there is a substantial excess of the designated stereoisomer. Preferably the other stereoisomer is not present in physiologically significant amounts, or is not present in any detectable amount.

These and other features, aspects, and implementations, and combinations of them, may be expressed as methods, apparatus, systems, program products, means for performing functions, compositions, purified entities, molecules, and in other ways.

Other aspects, features, and advantages will become apparent from the following description and from the claims.

DESCRIPTION

FIG. 5 is a table representing a separation sequence.

Figure 1:
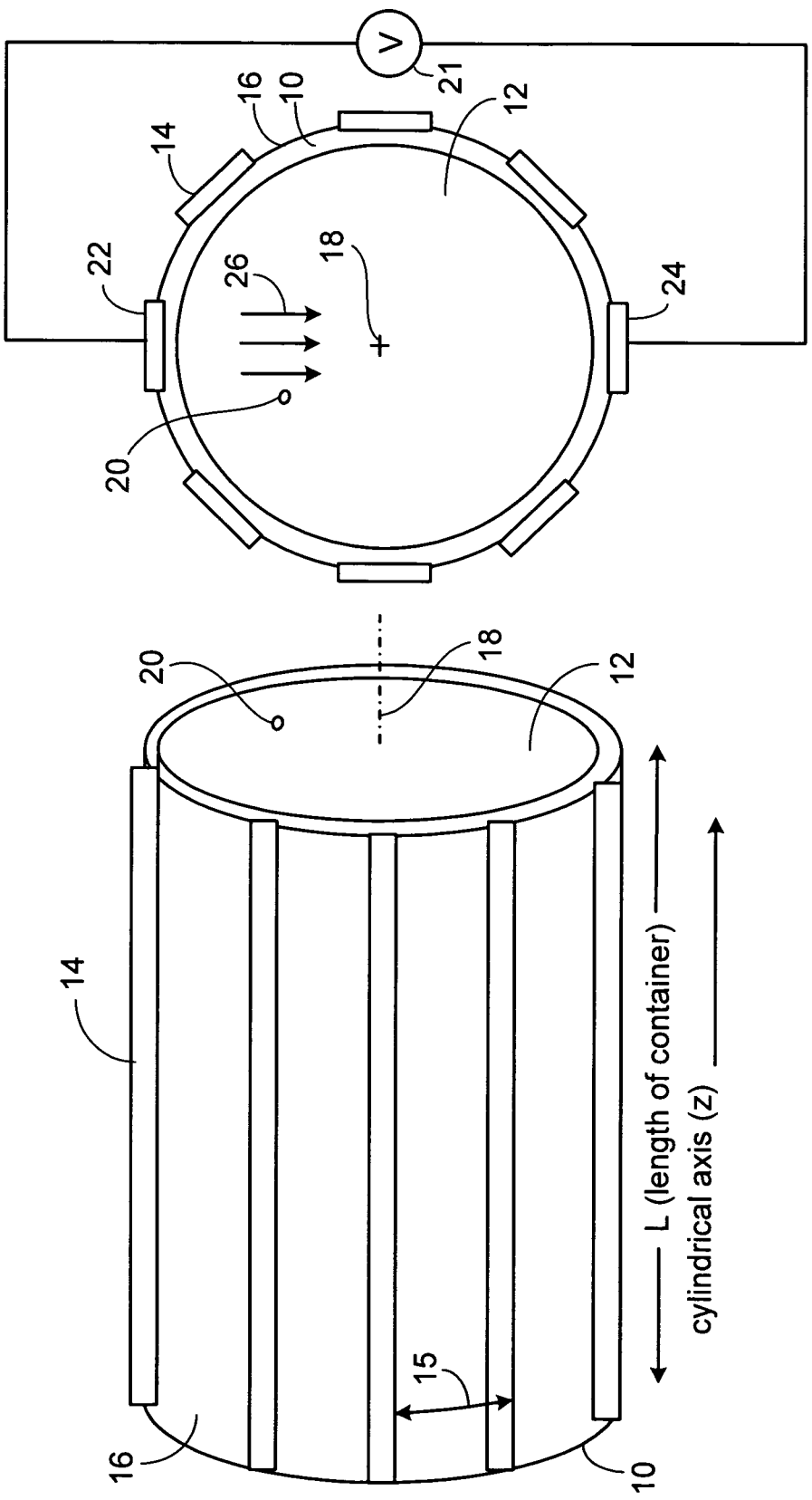
FIG. 1 is a perspective side view and an end view of a cylinder.

As we discuss here, separation and manipulation of chiral objects can be achieved without using chiral media, by relying on the susceptibility of the objects to external forces and the handedness of the objects. For example, the dipole moment that characterizes chiral molecules is susceptible to being rotated by a rotating external electromagnetic field. And the left handedness or right handedness of counterpart enantiomers, for example, can be used to transform the rotational motion of the enantiomers into translational (i.e., directional) motion of the two counterpart enantiomers in opposite directions. The helical handedness of some molecules, for example, is similar to the opposite handedness of left-handed and right-handed macroscopic propellers, which (when rotated) can propel themselves and objects to which they are attached in respectively opposite directions through a medium in which they are held.

The propeller of each molecule is characterized by the spatial configuration of its chiral features. As the propeller rotates, these spatial features act against the fluid resistance of the mixture that holds the molecules to force the propeller and the molecule to move in a direction. We sometimes refer to this transformation of rotational motion of the propeller into directional motion depending on the handedness of the propeller as the propeller effect.

In some examples, an external rotating electrical field is applied to a sample of chiral molecules. An electric dipole of each chiral molecule lines up with the external electric field and rotates with it causing rotation of the chiral molecule. The handedness (i.e., chirality or chiral features) of the molecule (which can be viewed as a tiny propeller) transforms this rotation into a linear (i.e., directional or translational) motion (E. M. Purcell, "The efficiency of propulsion by a rotating flagellum," Proc. Natl. Acad. Sci. USA, Biophysics, v 94, pp 11307-11311, October 1997).

At a molecular level and in a fluid (characterized by very low Reynolds numbers), inertial forces on the chiral molecules are negligible. The motion of the molecule that results from its rotation is similar to a left-handed or right-handed corkscrew motion. For a particular force applied by the rotation of the molecules in the mixture, the S and R enantiomers will acquire the same velocities but in opposite directions. Concentration gradients for both enantiomers will be established based on the magnitude of these velocities, compared to the inherent diffusive flux of the molecules in the mixture, which is characterized by the diffusion constant.

The magnitude and profile of the concentration gradient for each enantiomer, and thus, the enrichment achieved, will depend on the efficiency of the enantiomers' propeller (that is, the efficiency with which its spatial configuration is converted to a linear force on the molecule, which relates to the size, shape and orientation of the propeller, among other things), the effective length of the container that holds the mixture, how long the field is applied, the electric field strength, the frequency of rotation, and properties of the fluid in which the enantiomers are held in the mixture, among other things. We sometimes refer to the propeller efficiency as the propeller propulsion efficiency.

We describe how to use a propeller effect to separate or manipulate chiral objects (such as chiral molecules) that is relatively inexpensive (because it uses simple equipment), achieves relatively high throughput (i.e., reaches a higher purity in a shorter period of time), applies to a broad range of types of objects and molecules, and produces (arbitrarily) high purity levels.

We also describe how to amplify (if there is a need) the separation to reach the arbitrarily high purity level for one or both of the enantiomers, for example, without sacrificing other performance parameters. Note that, although we use enantiomers in describing some implementations here, the principles apply broadly to any chiral molecules or chiral objects.

In some implementations, to separate the counterpart enantiomers, a cylindrical (e.g., glass) container 10 (FIG. 1) is filled with a racemic mixture 12 (held in a fluid, for example, in solution in a solvent). Parallel stripes of longitudinal electrodes 14 are spaced at regular angular intervals 15 around the outer surface 16 of the container and are parallel to the longitudinal cylindrical axis 18. Each of the molecules 20 in the racemic mixture has a permanent electric dipole moment. We sometimes refer to the space within the container as a chamber. Although we often describe the chiral objects as being in a solution having a solvent, we mean to include by such references any kind of fluid or medium in which the molecules or other chiral objects may move.

Figure 2:
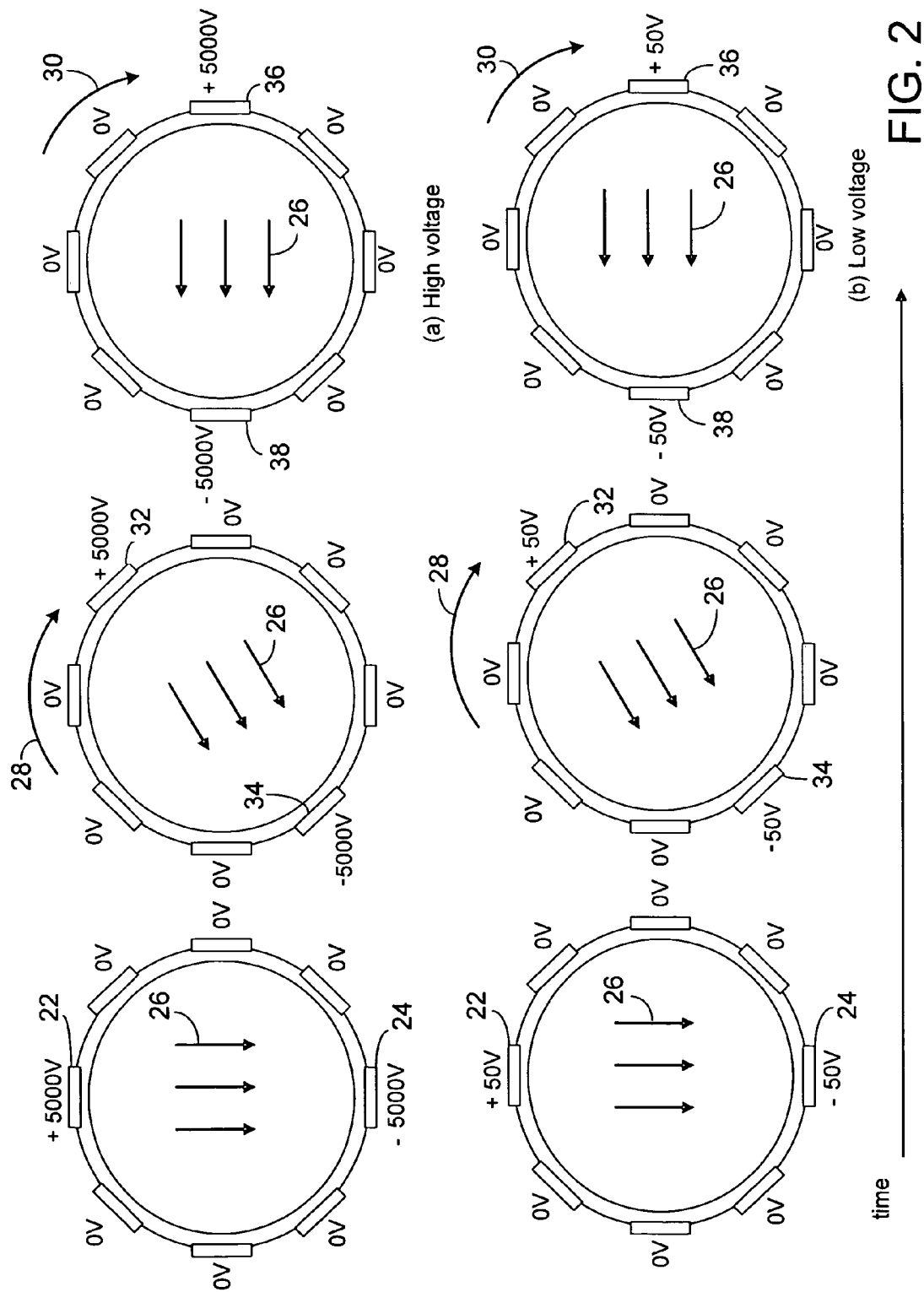
FIG. 2 shows schematic high voltage ((a), at the top) and low voltage ((b), at the bottom) profiles over time (left to right).

A voltage profile over time 21 is applied between pairs of the electrodes in sequence. First, two of the electrodes that are on opposite sides of the container (for example, electrodes 22, 24), which establishes an electric field (26) inside the container that causes the electric dipole moments of both enantiomers to align themselves with the electric field all along the length of the cylinder. The voltage is applied to a succession of pairs of electrodes on opposite sides of the container (FIG. 2). For example, electrodes 32, 34 receive the voltage at the middle times in FIG. 2 and electrodes 36, 38 at the later times in FIG. 2. Thus, in evenly spaced timed steps, the applied voltage (and the direction of the field induced by the voltage) rotates 28, 30 around the cylinder at a fixed rotational frequency (e.g., a number of rotations around the cylinder per second). The stepping of the voltage can be controlled to cause the rotational frequency to be in the kHz-GHz range or in specific sub-ranges of that broader range. In some examples, the rotational frequency could be varied over time.

The rotation of the external field causes a continuous torque to be applied to the dipole moment of each of the molecules, causing it to rotate with the field. In this example, both enantiomers rotate in the same angular direction. During rotation their chiral features (that is, the spatial features that represent their handedness) will act as tiny propellers. Of course, the right-handed and the left-handed chiral features of the molecules of the two counterpart enantiomers will cause them to behave respectively as oppositely handed propellers.

Rotation of the tiny propellers by the field-applied torque is transformed into translational motion (i.e., linear motion) of the two enantiomers in opposite directions. For example, if the right-handed molecules are propelled to the right end of the container, then the torque will cause the left-handed molecules to be propelled to the left end.

Figure 3:
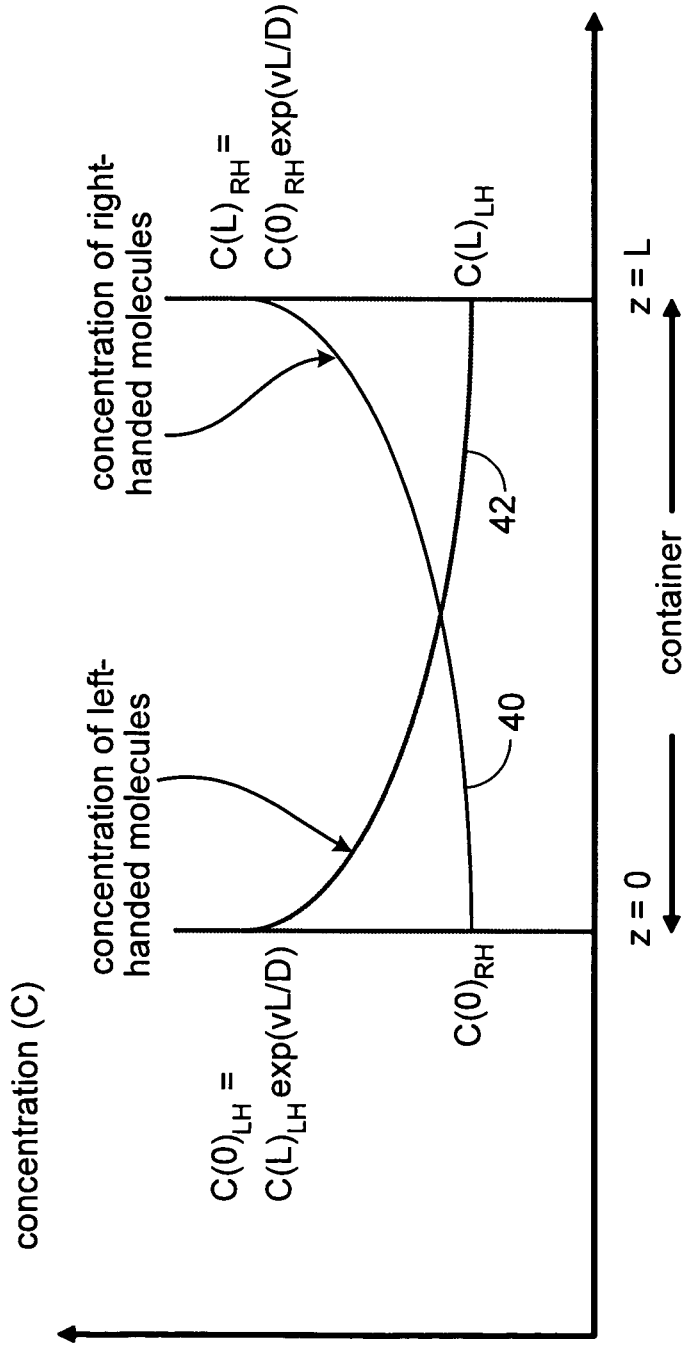
FIG. 3 is a graph of gradients.

Based on the strength and rotational frequency of the electric field, the molecule's dipole moment and its angle relative to the molecule's propeller axis, the solution properties, and other parameters, the two enantiomers will both move at a net velocity (v) along the cylindrical axis, but in opposite directions (i.e., one at +v, the other at −v). A concentration gradient 40, 42 (FIG. 3) will be established along the length L of the container (i.e., along the cylindrical axis) for each enantiomer.

The gradients for the respective enantiomers will be in opposite directions. If the right handed molecules have a velocity +v (traveling to the right), their concentration will increase towards the right; and vice versa for the left handed molecules. The magnitude of the concentration gradient that can be established for a given set of parameters will be limited by the diffusion constant for the molecule (given the properties of the setup, such as temperature and the choice of fluid in which the molecules are moving). After a long enough time (i.e., enough for diffusion or the enrichment to reach a steady state), the ratio of the concentrations of the enantiomers at the two ends of the container depends on a factor exp(+vL/D), where exp stands for exponential, v is the linear velocity of the molecule that is caused by the externally applied field, L is the effective length of the container, and D is the diffusion constant of the molecule in the particular solvent (although we sometimes use the word solvent, the principles apply to any fluid in which the molecules are held) in which the racemic mixture is dissolved. The formula for the steady-state concentration at an arbitrary position x is given by:

$$C(x) = C_{Ave} \frac{v \cdot L}{D \cdot (e^{\frac{v \cdot L}{D}} - 1)} e^{\frac{v}{D} \cdot x},$$

where $C_{Ave}$ is average concentration within the chamber, and x is distance from one edge of the chamber.

To understand how the propeller effect depends functionally on molecular parameters and experimental configurations, a rotational diffusive flux theory can be applied to calculate the efficiency of chiral separation using propeller motion. The efficiency of separation of enantiomer molecules depends on (1) the average distance traveled per one full revolution ($L_{rev}$), (2) the frequency of rotation (f), and (3) the magnitude of rotating electric field (E).

The factor $L_{rev}$ is determined by properties of the molecule, including its geometry, conformational state(s), orientation of its dipole moment with respect to its propeller axis, solvent, temperature, and viscosity, among others. According to our molecular dynamic simulations, $L_{rev}$ is typically in the range of 0.1 to 4 Å/per one revolution for most chiral molecules. $L_{rev}$ is basically a fixed parameter for a given choice of a chiral molecule and solvent combination (assuming solubility related issues are negligible).

Consequently, optimization of enantiomer separation (or manipulation) using the propeller effect depends on knowing (and using) the relationship of separation efficiency to the other two parameters (f and E). Because the molecular rotational relaxation time of a small molecule (the time it takes the molecule to rotate fully in response to the rotating electric field) is typically on the order of 1-100 ps in a solution (mixture) at room temperature, most of the small molecules should be able to follow rotation of the electric field at frequencies up to ~10 GHz. Therefore, the dependence of the average directional velocity resulting from the propeller effect on the rotational frequency of the field is expected to be linear up to ~10 GHz and (assuming f remains below ~10 GHz) can be expressed as $<v> = L_{rev} \cdot f \cdot F(E)$, (Eq. 1), where F(E) is a function that incorporates the dependence of the propeller effect on electric field strength.

It has been argued empirically that the dependence of the propeller effect on the electric field should be quadratic at low field magnitudes (Baranova, N. B. & Zeldovich, B. Y. Separation of Mirror Isomeric Molecules by Radio-Frequency Electric-Field of Rotating Polarization. *Chemical Physics Letters* 57, 435-437 (1978)), i.e., $F(E) \sim E^2$ for small E (where "small" refers to the ratio of a potential energy difference that the field can impose on the molecule (~μE, where μ is the electric dipole moment of the molecule) compared to $k_B T$ (the unit thermal energy). Baranova assumed (without proving) that the translational velocity of a molecule due to the propeller effect in a rotating electric field should be proportional to the product of the electric field and a time derivative of the electric field (equation 2a of Baranova).

Other later studies (Gelmukhanov, F. K. & Ilichov, L. V. Orientation of Stereoisomers by Electromagnetic-Field. *Optics Communications* 53, 381-384 (1985); and Evans, M. W. & Evans, G. J. The Effect of External Electric-Fields on Molecular Liquids and Induced Translational Motion. *Journal of Molecular Liquids* 29, 11-35 (1984). did not question Baranova's equation 2a. The Evans study interpreted the propeller effect as described by Baranova, as being due to "magnetic orientation of the particles in the field of circular polarization" even though Baranova only considered interaction at the electrical dipole level. The theoretical analysis in Baranova relied on a two-dimensional (2D) stochastic Langevin equation to describe a chiral molecule having electric dipole moment and exposed to the rotating electric field. The average translational velocity was found by perturbative solution of Langevin equation to the second order in the electric field which resulted in quadratic dependence on the electric field magnitude (equation 6 of Baranova).

We have now shown that the behavior of propeller motion in a rotating electric field can be solved exactly, without empirical assumptions, and that the result of the exact derivation is in direct contrast with Baranova's reasoning. We infer that the original empirical assumption (equation 2a of Baranova) is unjustified and therefore the conclusions of Baranova are incorrect and misleading. We have found complete analytical solutions for this problem both in 2D and in 3D cases, which are valid at any electric field strength.

The starting point for our analysis is a rotational diffusion equation for a molecule with a dipole moment exposed to a rotating electric field. We assume that the electric field rotational frequency is much lower than the rotational relaxation time (i.e., that the molecule can easily follow the field rotation). This enables us to use a stationary diffusion equation to find an equilibrium angular distribution of molecular dipole moments as a function of orientation and magnitude of the electric field. The solutions for function F(E) describing the dependence of the propeller effect on the electric field can be found using two approaches that yield virtually identical results.

The first approach relies on calculating the fraction of the molecules that are following the rotation of the electric field. This fraction depends on the temperature. At higher temperatures, this mobile or correlated fraction is smaller because molecules have more kinetic energy to escape from alignment with the electric field.

Another approach relies on calculation of a net rotational diffusive flux resulting from an infinitesimally small change in the orientation of electric field.

Our expressions for 2D and 3D cases are, respectively:

$$F(E) \approx 1 - \frac{1}{e^{\frac{\mu E}{k_B T}} I_0\left(\frac{\mu E}{k_B T}\right)} \text{ and} \quad (\text{Eq. 2})$$

$$F(E) \approx 1 - \frac{2\mu E}{k_B T\left(e^{\frac{2\mu E}{k_B T}} - 1\right)}, \quad (\text{Eq. 3})$$

where $\mu$ is the electric dipole moment of the enantiomer, $k_B$ is the Boltzman constant, T is temperature, and $I_0$ is a modified Bessel function of the first kind.

The solution of the 3D case should include the contribution to the propeller effect from preferential orientation of dipole moments in the plane parallel to electric field rotation plane; however, we have shown that this contribution is small (at most a factor of ~1.274 at weak fields) and therefore is not included in Equation 3. When interaction energy of the electric dipole moment with the electric field is small compared with $k_B T$ (i.e. $\mu E \ll k_B T$), equations 2 and 3 yield following asymptotic solutions:

$$F(E) \approx \frac{\frac{\mu E}{k_B T}}{1 + \frac{\mu E}{k_B T}} \text{ and} \quad (\text{Eq. 4})$$

$$F(E) \approx \frac{\frac{2\mu E}{k_B T}}{1 + \frac{2\mu E}{k_B T}}, \quad (\text{Eq. 5})$$

for the 2D and 3D cases, respectively.

Figure 29:
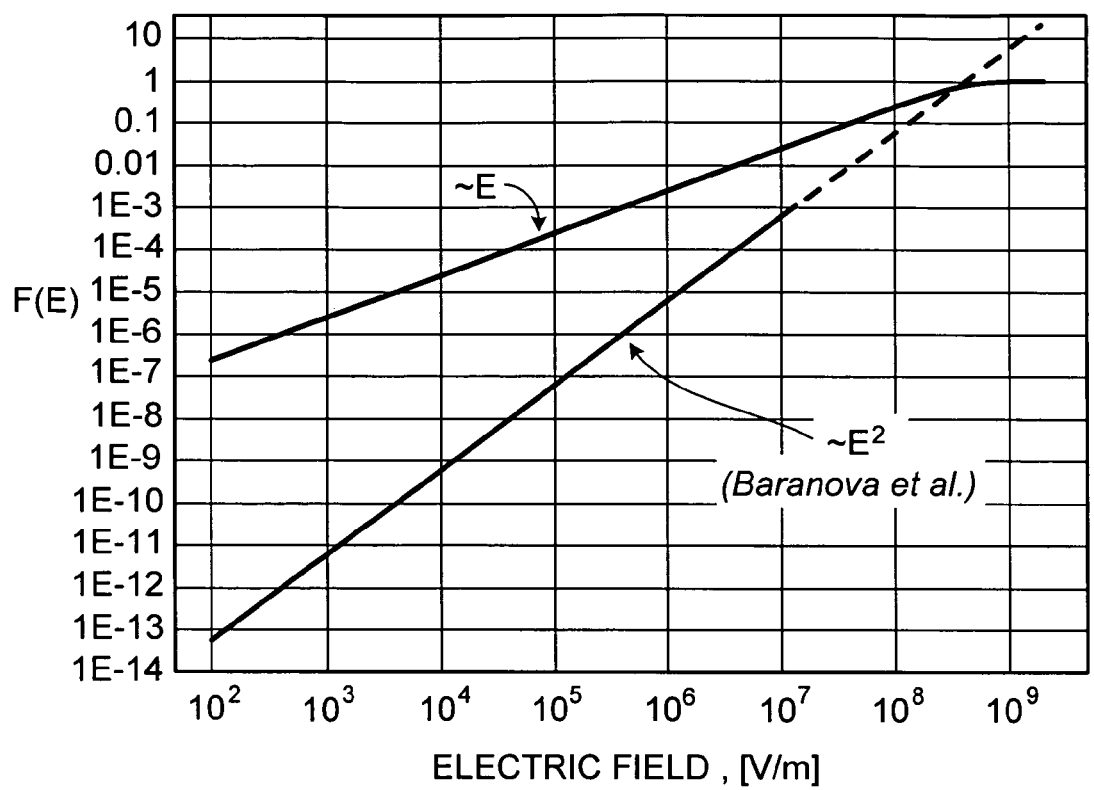
FIG. 29 is a theoretical graph.

These expressions indicate that, for small electric fields, the propeller effect varies linearly with the electric field magnitude. Thus, at low electric fields, the propeller effect is linearly proportional both to the frequency of rotation and to the magnitude of the electric field. In other words, in terms of optimization of the propeller effect, the rotational frequency and strength of the field are interchangeable variables (<v>~E×f). This result is in direct contrast to Baranova's conclusion that <V>~E²×f. Furthermore, this result indicates that the magnitude of the propeller effect at any practical electric field strength is much larger than what is predicted by Baranova's conclusion. A theoretical comparison of the two alternative expressions for F(E) as a function of E is shown in FIG. 29.

Our conclusion demonstrates, contrary to the implication of Baranova's reasoning, that the efficiency of the propeller effect can be improved by increasing the frequency of electric field up to the GHz range, even though the magnitudes of achievable electric field are low at such high frequencies. In other words, we have discovered that high propeller efficiencies (for example, propeller efficiencies at levels that can be used to produce economically practical separations) can be achieved in spite of the lower field magnitudes that are associated with producing high frequencies, as long as the decrease in electric field magnitude is compensated by an equivalent (e.g., the same amount of) increase in the rotational frequency factor.

This combining of low field magnitude and high frequency to achieve practical levels of efficiency would appear not to be possible based on Baranova's (incorrect) quadratic dependence of efficiency on electric field amplitude. From the quadratic dependence, it can be inferred that higher efficiency could be better achieved by a higher strength of the electric fields than by increasing the rotation frequency (which, in practical terms, is typically accompanied by lower field strength). Increasing the power of a microwave field, for example, would not be practical, because the power (~1 GW) needed to achieve the needed electric field magnitude ($10^6$-$10^8$ V/m) implied by the quadratic dependence would far exceed the amount of energy that could be released due to dielectric loss in the solvent (which would lead to unacceptable heating and even boiling of the solvent).

According to our expressions (Eqs. 4 and 5), however, electric fields as low as $10^4$ V/m can lead to efficient propeller motion, if the frequency of electric field rotation is increased proportionately e.g., to the 100 MHz-10 GHz range for such low fields, which are attainable using available electronic components and circuits. Then the voltage applied across the electrodes may be reduced while the rotation frequency of the electric field can be increased by the same factor to produce an equivalent linear velocity of the chiral molecules (i.e., similar or even higher <v> for the enantiomers). For example, a rotating field at 10 kHz generated by +/−5,000V is expected to be as efficient as +/−50V at 1 MHz.

Our theoretical and experimental analysis indicates that the propeller effect works even at low field magnitudes, so that the molecules can be rotated by a rotating electric field or a rotating electromagnetic field (i.e., a circularly polarized), within a broad variety of frequency ranges (e.g., RF, microwave, infrared, visible, UV, or other frequencies). If the applied field is electromagnetic, practical power levels (e.g., for which sourcing or heating is not an issue) that provide low electric fields, can be used, and the relatively lower molecule velocity resulting from these practical power levels can be more than compensated by an increase in the rotation frequency of the field (e.g., in the MHz range for RF up to GHz range for microwave). By using a rotating electric field at relatively low rotational frequencies (<1 GHz) and low power levels using, for example, a multiple electrode setup (FIG. 1), the absorption of energy from the externally applied field by the racemic solution (which can produce undesirable heating of the solution) is reduced or eliminated. This approach also simplifies the overall setup and decreases its cost, because the electric fields can be generated purely electronically.

For example, suppose a 2% composite enrichment of two enantiomer concentrations could be achieved over a 1 mm long container (i.e., a 51-49 ratio of the concentration levels of the two enantiomers at opposite ends of the container, and L=1 mm). The upper limit for the time period required for the enrichment to reach a steady state (in other words, the time after which further enrichment will no longer occur) is proportional to $L^2$ (i.e., $t_{steady-state} \simeq L^2/D$), so for L=1 mm and D~$10^{-5}$ cm$^2$/s, $t_{steady-state}$~$10^3$ s~half an hour. And if the characteristic length of the propeller effect (D/v) is significantly smaller than the length of the container (L) (i.e., D/v<<L), the time required for separation is given by ~L/v. The container length (L) could be increased to achieve any desired purity level. The time required for diffusion to reach steady-state increases quadratically with L. However, the displacement of the molecules due to the propeller effect is linear in time, while diffusive spread scales as the square root of time. Given sufficient time, linear motion always overtakes diffusion. Therefore high purity levels (e.g., 99%-1%) can be achieved in a sufficiently long container, without establishing concentration equilibrium.

Figure 4:
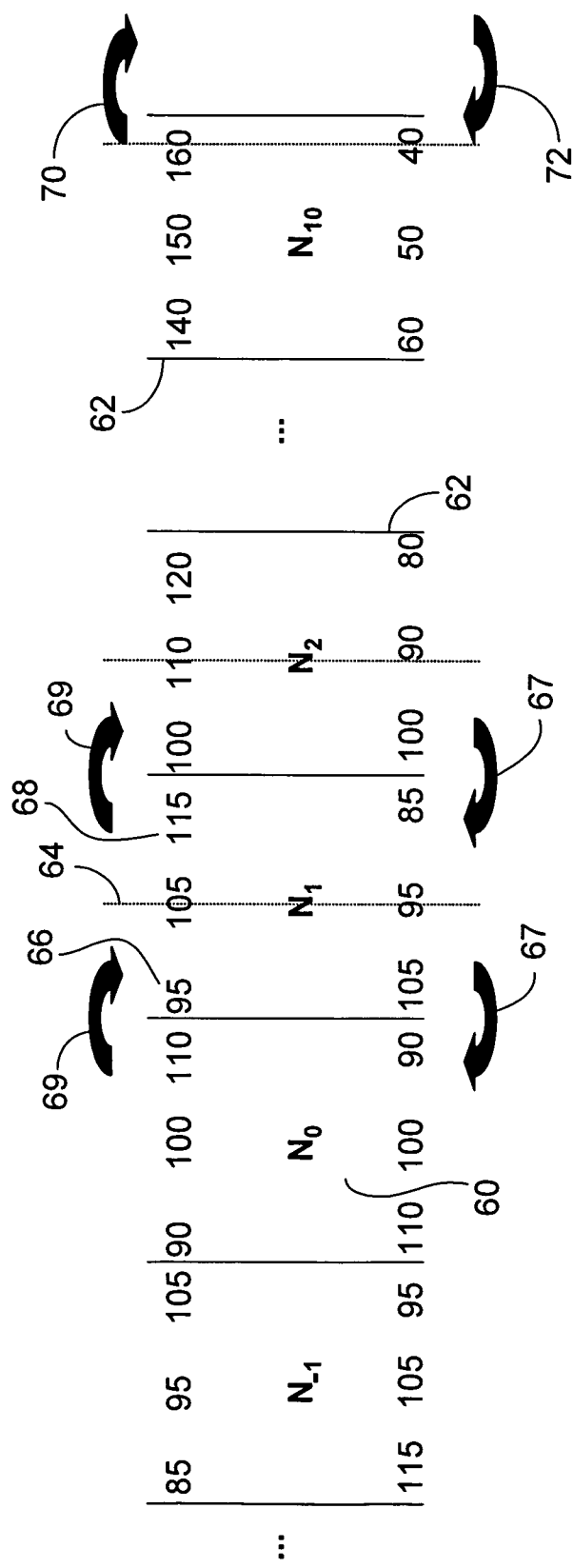
FIG. 4 is a schematic diagram of multiple separation chambers.

To achieve higher purities in less time, multi-step amplification can be used. One way to amplify an arbitrarily low purity level in one container to achieve an arbitrarily high desired purity level (within a reasonable amount of time) is shown in FIG. 4. In this example, we assume a linear concentration gradient (instead of an exponential one) for simplicity, but the amplification algorithm that we discuss may be modified for any type of gradient profile.

In this example, we have ~2N chambers, N=10, lined up consecutively and numbered from $N_{-10}$ to $N_{+10}$ (only some of them are shown). A strictly racemic mixture 60, of 50%-50% concentration, is in the middle chamber, $N_0$. Neighboring chambers are connected to each other using, e.g., pumps and barriers (not shown), and reservoirs (not shown) are operated for temporary storage of solutions obtained in a time succession of purification steps. During each purification step, the contents of each chamber are kept separate from the contents of its neighbors (i.e., the contents are not allowed to interact). In the times between successive purification steps, all or portions of each chamber's contents may be transferred to the next and/or to the previous neighboring chamber in the sequence.

Neighboring chambers are separated by walls 62. For purposes of describing concentrations of the enantiomers, each chamber has a middle point 64, a left point 66, and a right point 68. The numbers shown across the tops of the chambers in FIG. 1 represent concentrations of the right-handed enantiomer, for example, and numbers shown across the bottoms of the chambers represent concentrations of the left-handed enantiomer.

Initially each chamber contains a pre-determined average concentration of each enantiomer, e.g., an average concentration of 100 in $N_0$, 105 in $N_1$, 110 in $N_2$, (using arbitrary units for concentration levels). For example, in FIG. 4, in chamber $N_2$, the average concentration level of the right-handed enantiomer is 100-110-120, for an average of 110. We discuss the concentration levels of only one type of enantiomer, e.g., right-handed molecules, as their concentration levels are amplified along the chambers going from chamber $N_0$ to chamber $N_{+10}$. The concentration of left-handed molecules is being purified at the same time along the chambers towards the left (going from $N_0$ to $N_{-10}$). We will describe later how the initial concentrations in each chamber may be established in a brief setup time.

During each of a time series of separation steps, a rotating field is applied separately to each of the chambers as explained earlier. Assume that the applied field on each chamber creates a net force acting on the right-handed molecules (corresponding to a directional velocity of the molecules) that yields a concentration gradient of 20 (again, in arbitrary units) at the end the time period of a given step. So, at the end of the step, inside the $N_0$ chamber (with average concentration 100), the concentration of the right-handed molecules at the far left end of the chamber will be 90, in the middle will be 100, and at the far right end will be 110. For the next chamber ($N_1$), the average is assumed to be 105, and the gradient would go from 95 to 115; for $N_2$, the gradient has an average of 110 at the middle point, with 100 and 120 at either end, and so on.

During the purification time step that lasts for the period $t_1$, equal magnitude concentration gradients (of 20 concentration points in this example) would be produced in each chamber, centered at the average level for that chamber.

At the end of $t_1$, the volume of the solution that is in the left half (e.g., half 67) of each chamber is transferred 67 to the right half of the previous (next to the left) chamber. For example, the solution in the left half of chamber $N_1$, from the left end to the middle-point, including all the molecules in it, in which the concentration ranges from 95 to 105 for right-handed molecules and 105 to 95 for left-handed molecules, respectively, is transferred to the previous chamber, $N_0$. Similarly, the volume of the solution that is in the right half of chamber $N_1$ (from the middle-point to the right end, with levels ranging from 105 to 115 for right-handed and 95 to 85 for left-handed molecules, respectively), is transferred 69 to the left half of chamber $N_2$, and so forth. The average concentration of the half-volume transferred to $N_2$ both from $N_1$ and from $N_3$ is 110 and 90 for right- and left-handed molecules, respectively, the same as the average of the whole $N_2$ chamber before $t_1$. Similarly, the average of $N_0$ was 100 for both enantiomers, which is exactly the average of the right half-volume of $N_{-1}$, as well as the average of the left half-volume of $N_1$. Thus, the average concentration and the total volume in each chamber remain constant from one time step to the next.

In summary, each chamber generates a concentration gradient of 20 in each time step, and by moving portions of the solution (more generally the mixture) between neighboring chambers, a desired purity level can be achieved for volumes in chambers that are away from the center chamber. While each chamber imparts a relatively small amount of enrichment, operating multiple chambers in sequence can amplify the overall purification level significantly. An advantage of using a multi-step amplification setup (as opposed to a single, long container) is that the total time to reach a certain throughput will be reduced by a factor of ~N (i.e., the number of steps). The time is reduced by a factor of 10, because even though the number of steps increases by N, the time it takes for a single container to reach steady-state decreases by a factor of $N^2$ (because this time period is quadratic with container length). As a result, for an enrichment factor of X per chamber, each enantiomer will be enriched by a factor of $(1+X)^N$, so the overall purity level will be $(1+X)^{2N}$ (because the overall purity is equal to the product of both enantiomers' enrichment). As an example, for X=1%, a 99%-1% purification can be achieved with ~200 steps.

The enriched sample can be collected from the final chamber (i.e., $N_{10}$ in this example). At the end of each time step, there is no $N_{11}$ to which to transfer the right half volume of $N_{10}$. Instead, a small fraction of that $N_{10}$ volume is collected 70, and the same volume of racemic mixture is injected 72 into $N_{10}$. The partial amount of solution (with enriched enantiomers) that can be extracted from the last chamber is ~V/2N (i.e., throughput is V/2N per time step), where V is the volume of a single chamber (so V/2 is the volume of the upper half), and N is the number of amplification steps (10, in this example). Extracting this volume of solution and substituting the same volume of racemic solution keeps both the volume and the average concentration in the last chamber constant from one time step to the next. This scheme enables continuous purification (enrichment) of enantiomers.

The above description assumed that increasing average concentrations in the respective consecutive chambers are pre-established at the start. These concentrations can be set up initially within a short period of time as shown in FIG. 5. We first fill $N_0$ with a racemic mixture (the first row in the table), i.e., with concentrations of 100-100 for both the left-handed and right-handed molecules. We assume 10 (arbitrary) units of volume in each chamber. Then we run chamber $N_0$ for one time step (during $t_1$), transfer the upper half volume (which has average concentrations of 105 and 95 of right-handed and left-handed molecules, respectively) to $N_1$, and transfer the lower half volume (which has average concentrations of 95 and 105 of right-handed and left-handed molecules, respectively) to $N_{-1}$. After these transfers, $N_0$ is completely empty, and $N_1$ and $N_{-1}$ are each half full with their respective correct average concentrations (i.e., $V_1=V_{-1}=5$).

We then fill $N_0$ with a racemic mixture again (i.e., $V_0=10$) and repeat the process during $t_2$ (line 2 of the table, without any transfers from $N_1$ and $N_{-1}$). At the end of $t_2$, $N_1$ and $N_{-1}$ are filled (i.e. $V_1=V_{-1}=10$) with their operational average concentrations of the two enantiomers and $N_0$ is empty. We repeat the initial process (of filling $N_0$ with a racemic mixture), and at each time step transfer half of the volume of the outermost chambers (that are full) to their subsequent neighbors until all the chambers are filled. Note that the total time it takes to fill the whole setup is not on the order of $2^N$, since we can start doing multiple half-volume transfers in parallel as more and more chambers are being filled. Instead, the initial set-up time is linear with number of steps, on the order of ~4N, where 2N comes from the fact that it takes two time steps to fill the outermost chamber, another N because we need to wait a third time step before we can make a transfer out of the outermost chamber, and another final N to fill up all the half-filled chambers at the end of the initial setup. In FIG. 5, we can see that it takes three time steps to bring each additional chamber into operation in the system (so setup time is on the order of ~3N). We need a final stage $t_{13}$ for cleanup on the order of another ~N.

Figure 16:
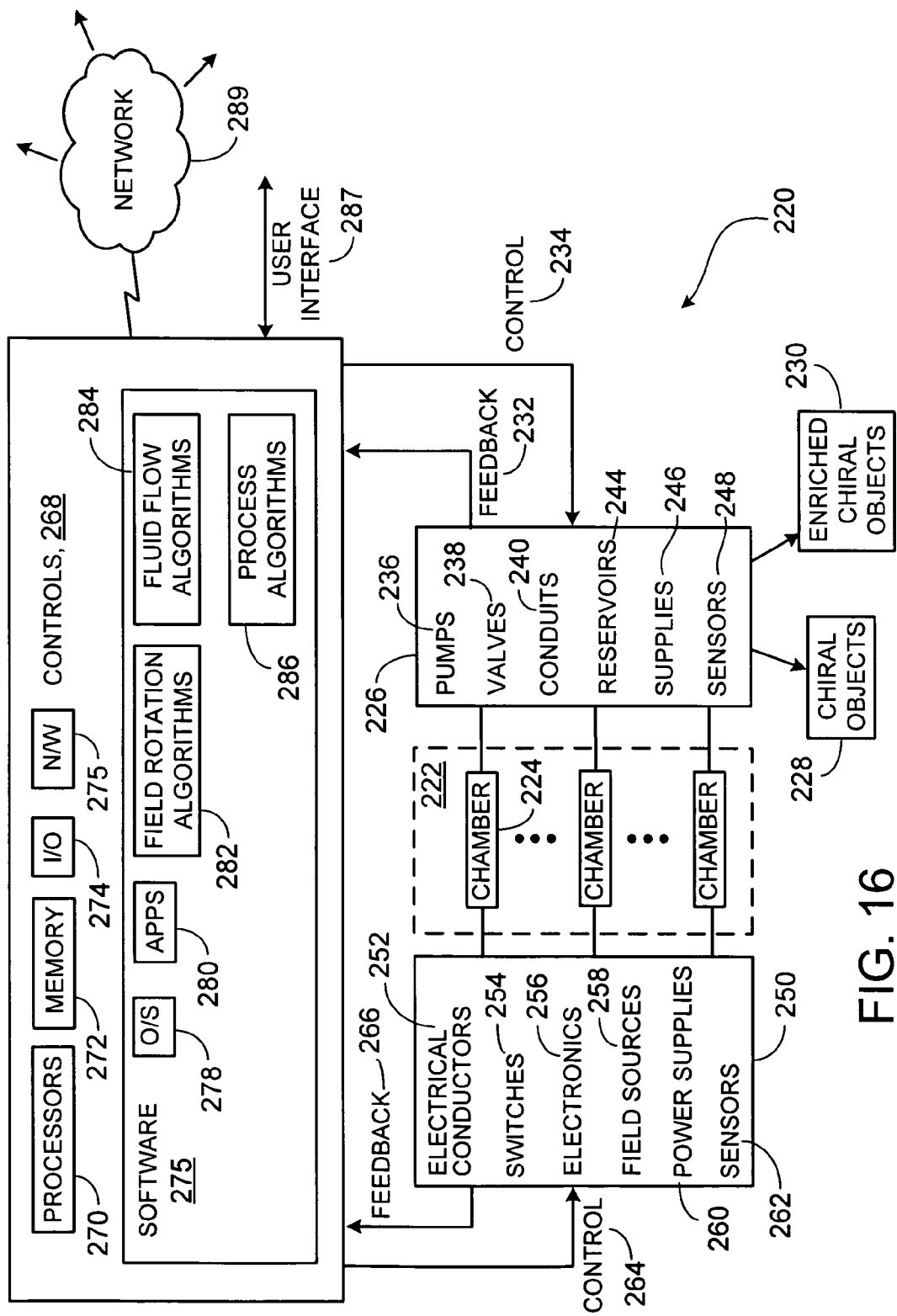
FIG. 16 is a block diagram

As shown in FIG. 16, a system 220 for receiving and processing chiral objects 228 and delivering, for example, enriched chiral objects 230 after processing, can include a set 222 of chambers 224, a fluid subsystem 226 and an electrical subsystem 250 both coupled to each of the chambers, and controls 268 that provide control signals 234, 264 to and receive feedback signals 232, 266 from the subsystems to cause the set of chambers to safely, efficiently, effectively, and quickly produce the enriched chiral objects.

In the fluid subsystem, reservoirs 244 temporarily hold supplies 246 of fluids, chiral objects, enriched chiral objects, and volumes of fluids that are passed from chamber to chamber during processing. The fluids are moved in and out of reservoirs and along conduits 240 and through valves 240 by electrically controlled pumps 236 based on the control signals from the controls. Sensors 248 can detect the presence, movement, velocity, volume, and composition of any of the fluids, chiral objects, or other materials that are present in or moving through the system. Corresponding feedback signals can be sent back the controls.

In the electrical subsystem, voltages to drive electrodes in the chambers are provided by power supplies 260 (which also power other components in the electrical subsystem, the fluid subsystem, and the controls. Other kinds of fields can be produced by field sources 258. Power is routed along electrical conductors 252 through controlled switches 254 and can be filtered, enhanced, and otherwise processed by electronics 256. Sensors can detect the voltages, currents, field strengths, rotational velocities, timing, and other characteristics of all electrical parameters and provide corresponding feedback signals back to the controls. The control signals control the operation of the power supplies, switches, field sources, electronics, and sensors.

The controls 268 may include processors 270, memory 272, network connections 275, input/output interfaces 274, and software 276, among other things. A user interface 287 enables a user to observe and control the operation of the system. The software 276 includes an operating system 278, database and other applications 280, field rotation algorithms, fluid flow algorithms 284, and process algorithms 286. The controls can communicate with other devices and users through a network 289.

In other parts of this description, references to software include, for example, portions of software 276 in FIG. 16.

A wide variety of modifications and enhancements to features described above are possible, including, for example, the following:

The chiral objects may be, for example, chiral molecules, stereoisomers, enantiomers, epimers, or aggregates of a number of chiral or achiral molecules. These chiral molecules may be, for example, drug molecules, drug intermediate molecules, sugars (such as monosaccharides, disaccharides, oligo- and poly-saccharides (glycans)), proteins, peptides, glycoproteins, glycolipids, or other macromolecules. The chiral objects may have one stereocenter or more than one stereocenter.

There may be only one type of chiral object in the mixture, or two, or more than two.

The molecules may belong to different categories, classified based on their various features, e.g., side groups, number of stereocenters, molecular size, 3D shape or structure, or interaction with the solvent or other fluid.

The proposed method may be used to analyze the chirality of the objects, to detect their presence and/or absence, or to separate two or more types of chiral objects.

Molecules may have more than one stereocenter. Molecules with more than one stereocenter may be separated into two groups or they may be separated into multiple groups (one for each stereocenter combination). These multiple peaks may be monitored (i.e., detected and/or analyzed) in real-time or as an end-point.

Epimers may be separated based on different rotation frequencies and/or different effective velocities they experience in response to the same applied field, even if their velocities have the same sign (i.e. even if their linear motion is in the same direction).

The applied field may be an electric field or a magnetic field.

The applied field may be rotated around a stationary chamber, or conversely, the orientation of the field may be fixed (i.e., static electric field or linearly polarized electromagnetic field) and the chamber may be rotated.

The mixture may be racemic, non-pure, or enantiopure.

The applied field may be generated by electrodes arranged around the chamber or it may be a field component of an electromagnetic beam (e.g., that is collinear with the chamber). The rotation frequency of the field may be less than 1 kHz, between 1-10 kHz, 10-100 kHz, 100 kHz-1 MHz, 1-10 MHz, 10-100 MHz, 100 MHz-1 GHz, 1-10 GHz, or above 10 GHz. It may be in the RF range or in the microwave range.

The separation of the two chiral objects may continue until the concentration gradient reaches steady-state (the longer we continue, the more stable the gradient will be). Or a time-gated cutoff scheme may be used, in which the molecules are released from a particular point in the chamber (e.g. one end of it, or from the mid-point). Then the chiral objects diffuse across the length of the container (with different velocities depending on their handedness) for a selected period of time, at the end of which the diffusion is stopped (either by terminating the applied field or mechanically) and the molecules are collected from a region where the desired purity is reached (e.g., from the tails of the distribution profiles). Note that the higher the desired purity, the lower the yield.

The time period applied may be adjusted to trade off enrichment consistency and throughput. That is, the longer the processing time, the more stable the concentration gradient will be (i.e., lower statistical noise in concentration levels), but the throughput will also be lower because the same quantity of material will be enriched over a longer period of time.

The concentration gradient profile may be exponential, linear, or non-linear.

The non-exponential profiles may be obtained by using separation parameters that are not constant along the length of the chamber (e.g. field intensity, rotation frequency, solution properties such as viscosity, pH, or co-solvent concentration).

The v/D ratio (i.e., velocity of a molecule divided by its diffusion constant) may be improved (i.e., increased) by attaching a chemical molecule (e.g., a chiral label) to the molecules of interest to enhance the propeller effect (e.g., by increasing the molecule's dipole moment and/or its rotational-translational coupling factor). Such chiral labels may also be attached to improve other system properties (e.g., noise, yield, purity, throughput).

The v/D ratio may also be improved (i.e., increased) by causing the molecules to experience a collective motion, in which they "sense" each other and act in unison (so that the net force acting on the respective molecules is additive, and yet, the diffusion constant acting on the aggregate is relatively smaller). This collective behavior may be accomplished using chemical (e.g., liquid crystal-like) techniques or physical techniques (e.g., ferromagnetism), or combinations of them.

The molecules may be in solution, in gas, or in high pressure fluid (e.g., supercritical $CO_2$, $N_2$, or Argon).

Different solvents may be used inside the container. These include polar solutions, e.g. water, polar organics (e.g., ethylacetate, acetonitrile, dimethylformamide (DMF), dimethylsulfoxide (DMSO)), alcohols (R—OH, with R=$C_n$), dichloromethane (DCM), methoxymethylether, tetrahydrofuran (THF), and the like, and nonpolar solutions, e.g. carbontetrachloride ($CCl_4$), alkanes such as cyclohexane, hexane or pentane, and the like. Solvents may have different thermodynamic properties (e.g., temperature, pressure) or physiochemical properties (e.g., different buffers, concentrations, pH, molecule solubility, ionic strength, viscosity, osmolarity).

The solvent composition may be adjusted (e.g., pH level) to optimize the propeller technique (e.g., neutralize the molecules to ensure a zero net charge per molecule).

If the solvent is polar (e.g., the solvent molecule has a permanent or an induced electric dipole), the solvent molecules may be rotated with an applied electric field, which in turn will impart angular momentum on the molecules of interest (polar or non-polar). And with this angular momentum, the molecules of interest may rotate and experience linear motion based on their chirality, as described previously.

The separation may be accomplished in a solution that is flowing in the chamber along its length or in a steady (non-flowing) solution. For a particular application, a counter-flow may be set up inside the container to oppose the propeller force, to set an opposing threshold for the molecules to overcome.

Figure 6:
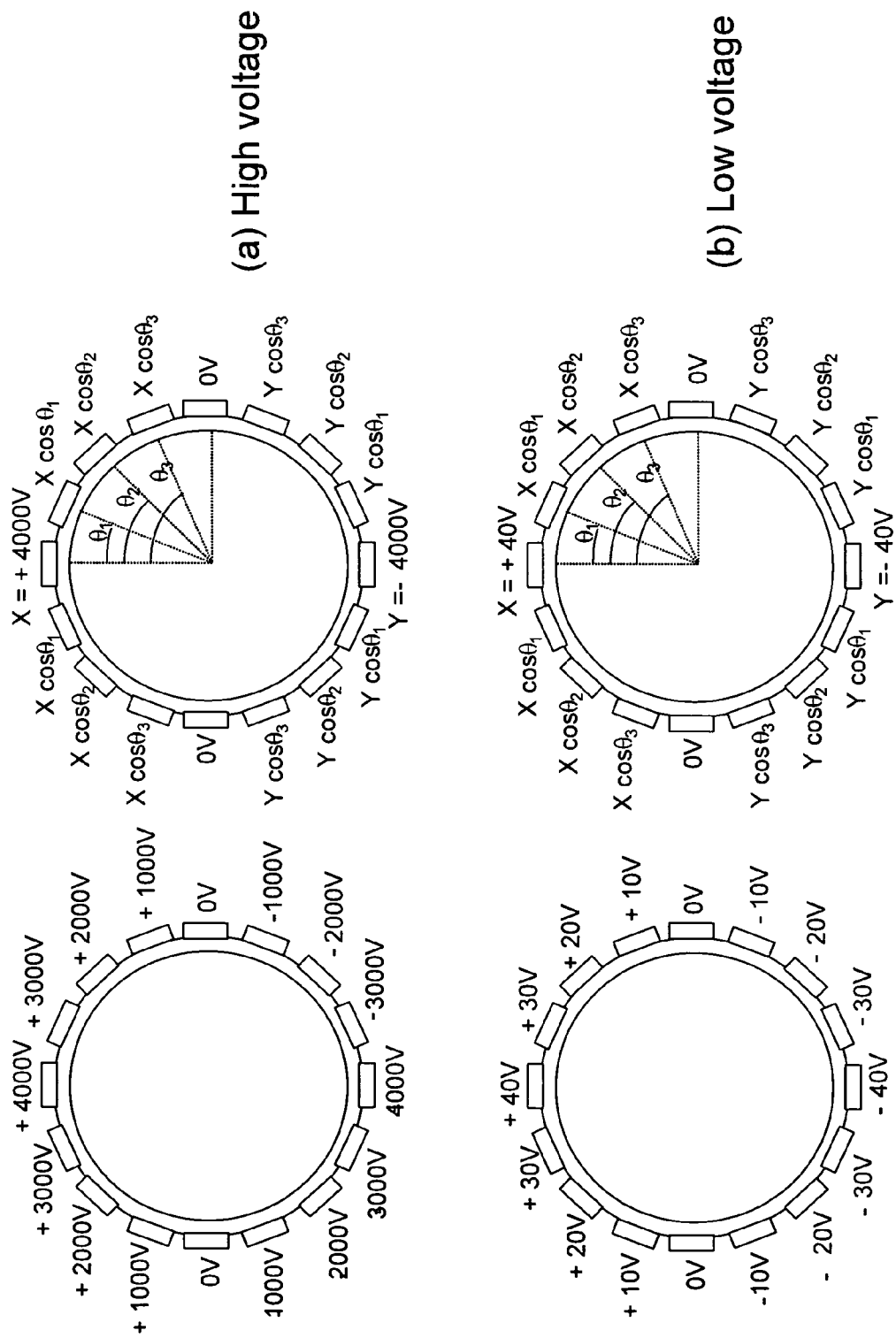
FIG. 6 shows schematic linear (left) and trigonometric (right) profiles using high voltage ((a), at the top) and low voltage ((b), at the bottom).

The effective electric field profile inside the container may be modified and controlled. This may be accomplished by a fixed parameter (e.g., shape of the tube, inner and outer diameter of the tube, material type, solvent conductivity, or pH) or by an adjustable parameter (e.g., by adjusting the applied field frequency along the z-axis, or apply a particular voltage to each electrode around the ring, rather than applying only the peak voltage to only the two opposing electrodes). Two example voltage profiles (linear and trigonometric on the left and right for high voltage on the top and low voltage on the bottom) are shown in FIG. 6.

The purification may be carried out in a predefined unchanging mode (e.g., automated, with no feedback), or it may be controlled and/or calibrated using real-time detection of the concentrations (or other parameters) of the output (or other portions of the mixture) for feedback.

The setup may have only one chamber or many chambers. It may have one sequence of chambers or many sequences running in parallel. One goal is to achieve a particular purity level in the shortest time possible (i.e., maximize throughput).

The enrichment may be carried out in only one direction (i.e., concentration of only one enantiomer is increased) or in both directions (i.e., both enantiomers are purified).

All chambers in a sequence may be of the same size or of different sizes (e.g., to account for concentration non-uniformities).

From one chamber to the next, only the molecules may be transferred or the whole volume of solution (fluid mixture) may be transferred.

Exactly half of each chamber's volume may be transferred to the next chamber or a volume that is less than half of the chamber may be transferred (i.e., a portion of a particular chamber's volume stays in that chamber).

The same volume may be transferred in both forward and backward directions (i.e., symmetric transfer) or the volume transferred forward may be different from that of the backward transfer (i.e., asymmetric transfer).

Depending on the concentration gradient profiles, different algorithms may be employed to improve a particular parameter of the system (e.g., purity level, purity consistency, shortest initial setup time, overall throughput, throughput within a fixed amount of time, for example).

Figure 7:
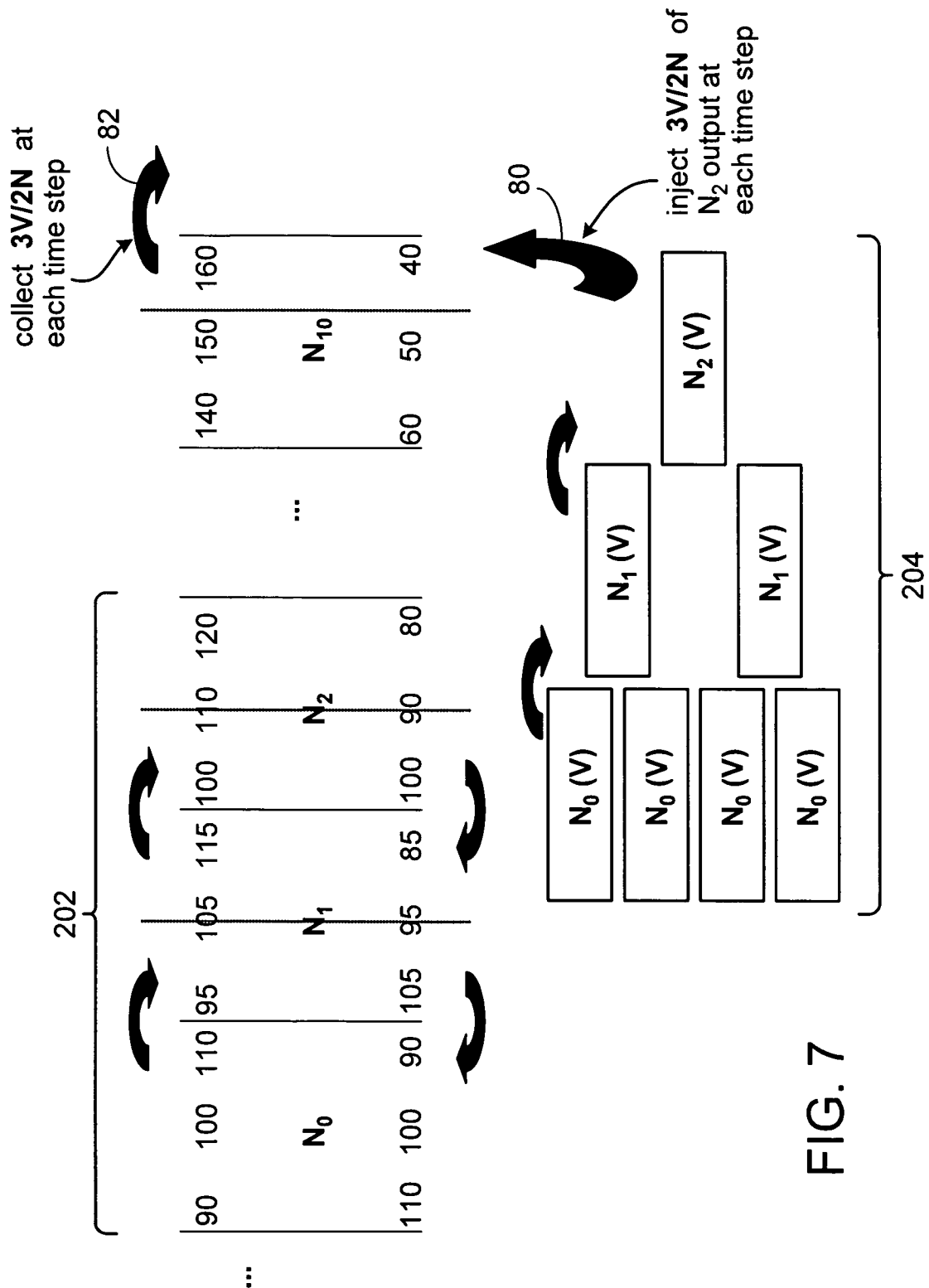
FIG. 7 is a schematic diagram of multiple separation chambers.

For a given sequence of chambers, additional chambers may be operated in parallel to increase the overall throughput. In the example of FIG. 7, the first three chambers 202 are replicated 204 (in addition to the original set of chambers; in this case four replications of $N_0$, two of $N_1$, and one of $N_2$), and a portion of the replicated $N_2$'s output is directly injected 80 into the final collection chamber (instead of a racemic mixture). Then three times the volume can be extracted from the last chamber for each time step (i.e., throughput is increased by a factor of 3), while keeping the average concentration of the last chamber constant after each time step. The replicated chambers could supplement the purification of the chambers at the beginning, at the end, and/or in the middle of the sequence. These replicated chambers may be provided for only one chamber or multiple chambers in the original setup.

The concentration gradients in each chamber may be initially established by incremental and sequential processing (as in FIG. 5), or simultaneously for many or all chambers. The required average concentrations also may be established externally and then loaded into multiple chambers simultaneously.

This initial establishing of the gradients may be automated or it may be calibrated by feedback using real-time detection and monitoring of the output (or other portions of the solutions).

The solution and/or the molecules may be input to each container and/or collected from each container (after enrichment) using various pumping mechanisms (e.g., mechanical, pressure, or membrane).

The detection and monitoring of the output may be done optically (e.g., by circular dichroism, optical index birefringence, optical absorption, or fluorescence), chemically (e.g., by chemical sensors or chiral columns or selectors or mass spectroscopy) or electronically (e.g., by chirally selective electrodes). It can be done in real-time or at an end-point of the processing.

The system (for example, the software 276 of FIG. 16) may include software to control, manage, or compliment the results. It may also include software to calculate and/or predict expected performance or performance limits, or average velocity of the chiral objects, or the direction of motion for each absolute configuration of a chiral object.

The system may be a fully automated, turnkey system. It may include features or modules such as sample preparation, auto-sampling, microfluidics, and fraction collection.

The system may control and/or optimize the environmental parameters (such as temperature or pressure). These parameters may be adjusted by hardware or software, and by online/remote access.

The system may automatically optimize or calibrate or monitor the various control parameters (e.g., applied voltage, frequency of rotation, duration of the applied field, which solvent to be used) to optimize the performance parameters (e.g., purity, throughput, yield, total run-time, multi-step amplification).

The system may optimize or monitor the reliability, repeatability, and reproducibility of the various runs.

The system may allow and/or manage multiple runs in parallel or in series, with different samples, solvents, or function and application.

The environment (the fluid, solution, or mixture) for the molecules may be asymmetric or anisotropic in at least one dimension (e.g., an anisotropic gel).

Various diffusion and convection reduction techniques may be used in the solvent, fluid, medium, or mixture (e.g., gel technology, bead technology, orientation of the chamber). Properties of the medium may be changed (e.g., packing with C18 bonded silica and/or porous versus nonporous media).

The propeller effect may be used at a small scale (e.g., microscale) or in a large scale (e.g., batch size). The chamber may be in macroscale, microscale, or nanoscale.

The container cross-section may be circular, rectangular, triangular or some other geometry, to enable practical electrode deposition and to achieve an optimum electric field profile inside.

If the applied field is a rotating electric field, the electrodes may be placed on the outer surface or on the inner surface, and, for the latter, they may be in contact with the solution or they may be laminated so as not to be in contact with the solution.

The electrodes may be of various materials (e.g., metal, semiconductor), types, or shapes (e.g., rectangular, spherical, etched radially outward from the center of the cylinder), and their characteristics may be selected to optimize the electric field profile and properties (e.g., improve the breakdown voltage).

The number of electrodes may be reduced to lower the cost of the electronics or it may be increased to achieve a more uniform electric field profile inside the container.

Figure 8:
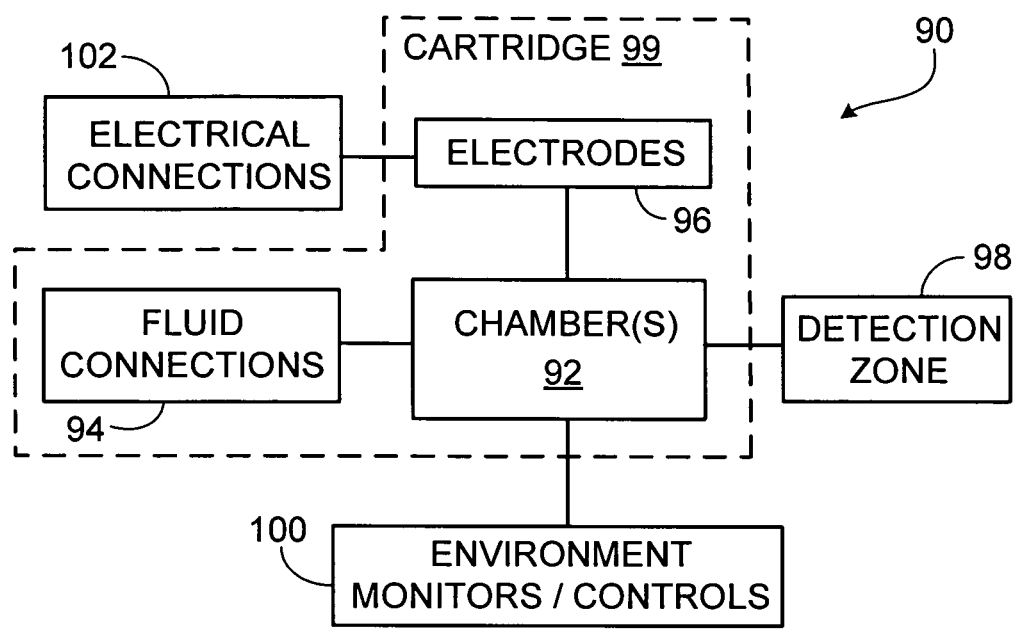
FIG. 8 is a block diagram.

As shown schematically in FIG. 8, chambers 92 can be implemented by providing electrodes 96 (and electrical connections 102), fluid connections 94, environmental monitors and controls 100, and detection zones 98. Depending on the application, these components can be manufactured in very high volumes, assembled in combinations and sub-combinations, and delivered as complete systems, or as modular sub-systems that can be combined in a wide variety of combinations by the user. The sizes, configurations, materials, costs, and scale of the components, and the sub-combinations and combinations of them can vary depending on the application. In particular, individual components, sub-combinations, and combinations can be produced in inexpensive, disposable forms, and we sometimes call these disposable components, or simply disposables. We also sometimes refer to components or sub-combinations of them (for example, a chamber with its electrodes and fluid connections, or a set of chambers with their electrodes and fluid connections) as cartridges 99. Cartridges can be disposables. In some examples, a cartridge, therefore, may include (a) a chamber or chambers 92 to hold the sample (we sometimes use the word sample to refer to a volume of fluid or solution that contains chiral objects), (b) electrodes 96 arranged about the chamber or chambers to produce a rotating electric field, (c) fluid interconnections 94 to inject and extract the sample or portions of it from the chamber or chambers, (d) a detection zone 98 to monitor the concentration of the sample or portions of it, (e) a device or devices (e.g., local sensors) 100 to control/monitor environmental parameters (e.g., pressure, temperature), and (e) electrical interconnections 102 to make electrical contact with the electrodes.

Figure 9:
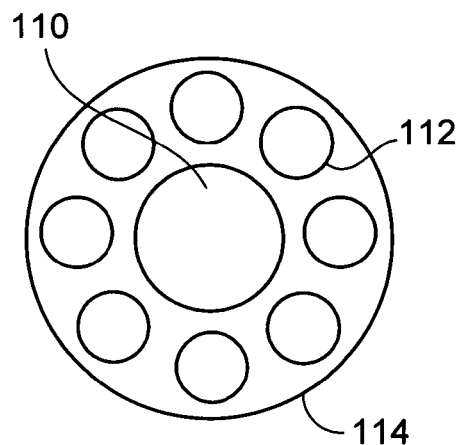
FIG. 9 is a cross-sectional view of a chamber.

High volume manufacturing techniques could be used to produce cartridges. For example, the chamber cross-section may be circular, rectangular, triangular, or some other geometry, to enable practical electrode deposition and to achieve an optimum electric field profile inside. As shown in FIG. 9, the sample chamber(s) 110 may be a capillary or capillaries. The capillaries may be of various materials (e.g., glass, polymer, quartz), and they may be coated on all or part of the inside surfaces. The sample chamber may be a microfluidic channel on a chip, formed by photolithography or by laminating multiple layers of material or a combination of both.

The electrodes 112 may be placed around the sample chamber and oriented axially (that is, with the long dimension of each electrode parallel to the longitudinal axis of the chamber) so that the enantiomers move (and the fluid in which they are held flows) longitudinally (along the axis). In some examples, the electrodes may be oriented orthogonally to the longitudinal axis of the chamber so that the enantiomers move transversely to a direction of flow of the solution or fluid during separation (e.g., across a Y-junction). The electrodes may be placed about the sample chamber at an angle that is neither parallel nor orthogonal. One or more of the electrodes may be an alternating current driven coil that causes the enantiomers to move longitudinally to the direction of flow of the fluid when the wavelength of the AC field approximates the coil diameter. A tubular ground shield 114 can be placed to surround the electrodes.

Figure 20:
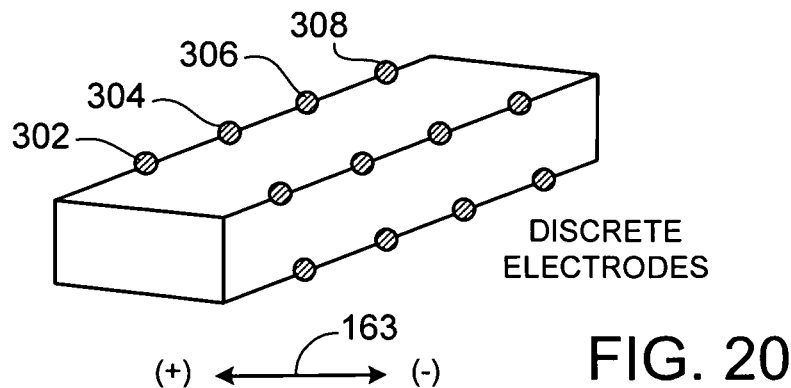
FIGS. 20 and 21 are a schematic perspective view and a schematic sectional side view of a chamber.
Figure 21:
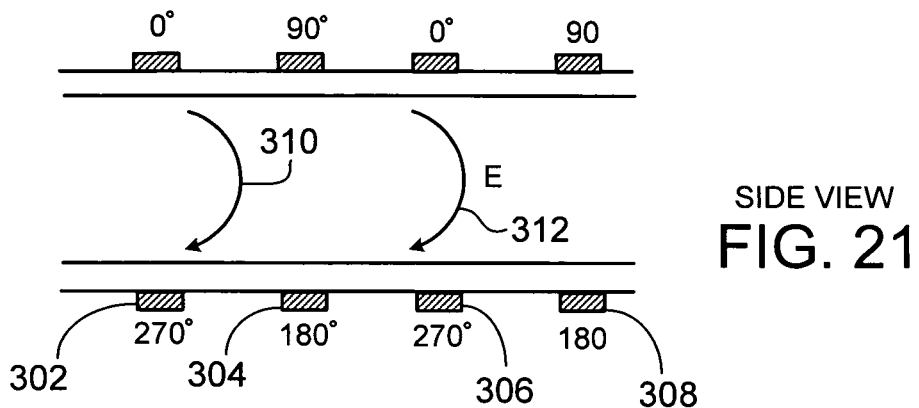

The sample chamber may bear a continuous set of electrodes that extend along the full length of the chamber and generate a uniform field across the chamber all along its length. As shown in FIGS. 20, 21, in some examples, the sample chamber may bear discrete sets 302, 304, 306, 308 of electrodes (each set occupying only a particular sub-length along the length of the chamber). Different sets of the electrodes can generate rotating electric fields 310, 312 having the same or different parameters.

Instead of using electrodes, a rotating electric field may be generated by circularly polarized microwaves that are propagated axially along the sample chamber, which acts as a waveguide.

Figure 22:
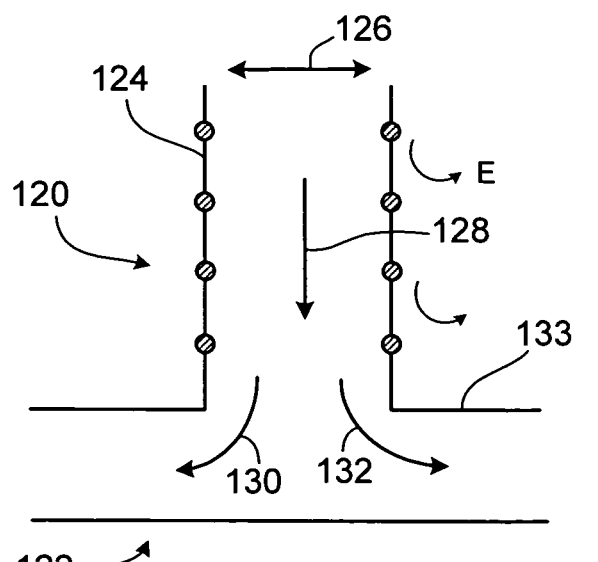
FIGS. 22 and 23 are schematic views of a T-junction chamber and a tree of T-junction chambers.
Figure 23:
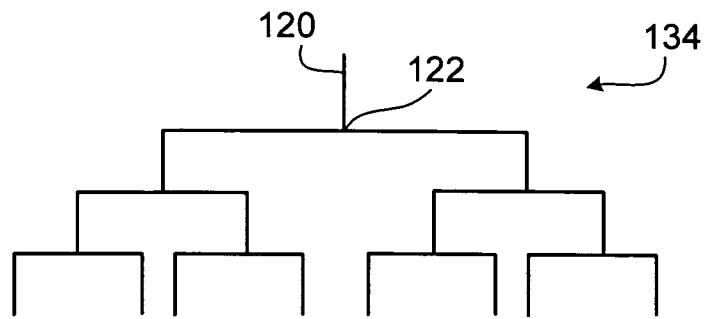

As shown in FIG. 22, in some ways of manufacturing cartridges, a chip can bear multiple chambers 120, each ending in a T- or Y-junction 122. Electrodes 124 on each chamber generate a transverse rotating field 126 relative to a direction of flow 128 of the solution (or fluid). In such an arrangement, the enantiomers are enriched along the edges of each sample chamber by the propeller effect and then are physically separated 130, 132 at the junction and drawn away in two opposite directions along a conduit 133. As shown in FIG. 23, this configuration may be repeated 134 on a single (or multiple chips) and organized in a tree to achieve a desired enrichment factor.

The disposable cartridge may be compatible with available liquid chromatography instruments that have appropriate fluidic interconnects. Typical connections may be luer or screw fittings.

Figure 10:
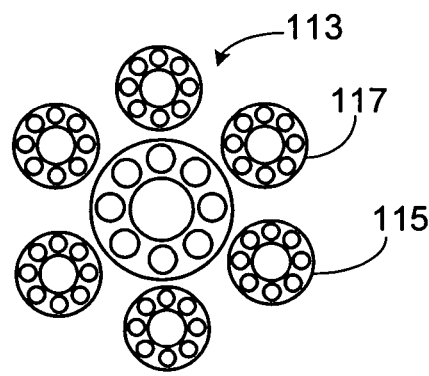
FIGS. 10 and 11 are a cross-sectional view and a side view of a bundle of chambers.

For example, returning to FIG. 9, a capillary 110 may be surrounded by a set of electrodes 112. The assembly may be held together by larger tubing 114. For high frequency operation, the tubing may be metal to serve as a ground shield. For high voltage operation, the larger tubing may be a dielectric material. As shown in FIG. 10, two or more of the assemblies of FIG. 9 may be grouped to form a bundle 113 of sample chambers with electrodes 115, 117 (we sometimes call the bundle a column). Hexagonal close packing is a possible geometry for the column.

Figure 11:
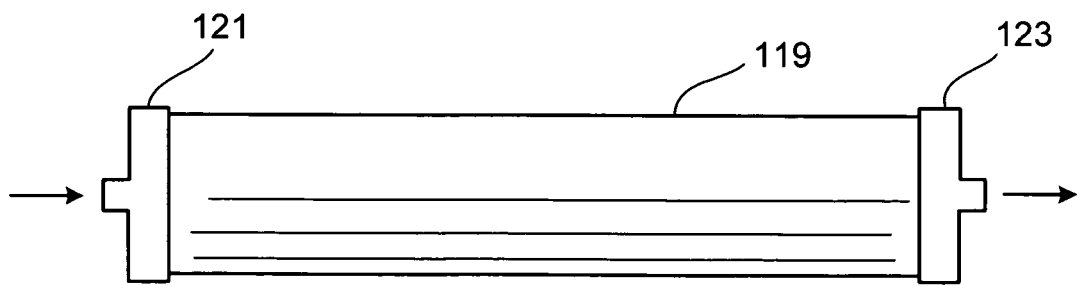

As shown in FIG. 11, the capillaries could be bundled together in a column 119 and terminated in luer fluidic fittings 121, 123, for example, to form a disposable cartridge that could be plugged into and removed from a larger system easily.

Figure 12:
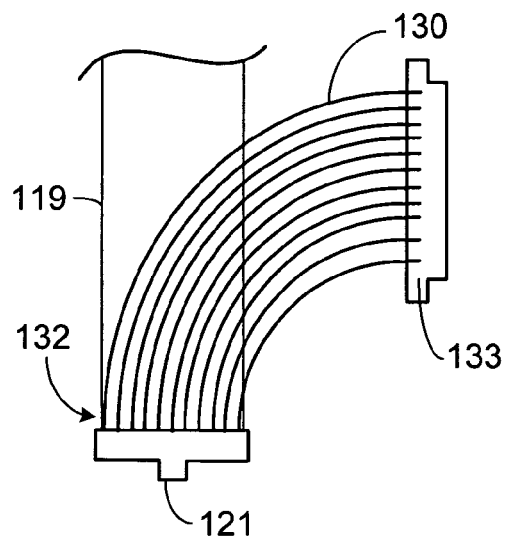
FIG. 12 is a top view of a wire bundle.
Figure 13:
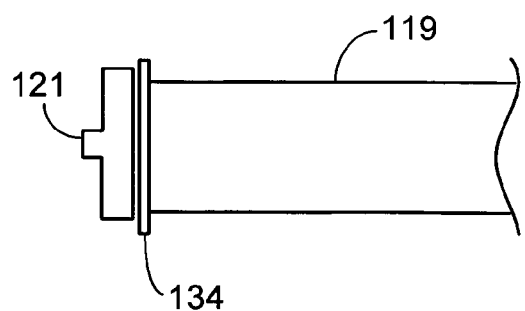
FIG. 13 is a top view of a connector.

Electrical connections between the electrodes of the cartridge and a source (not shown) may be made by a set of bundled wires 130 (FIG. 12) that are permanently connected to the electrodes at the column (and in that case part of the disposable cartridge) and have a connector 133 at the source end. As shown in FIG. 13, in some examples, the connections can be made through rigid or flexible printed circuit boards 134, or elastomeric connectors that are part of the disposable cartridge.

The conductors can be terminated at one or both ends by adapters for easy connection or disconnection (plug-n-play). Such a column 119 containing one or more capillary assemblies, fluidic connections, and electrical connections could be made in large quantities as a disposable cartridge and multiple copies of the disposable cartridge could be assembled to form a complete separation device.

Figure 14:
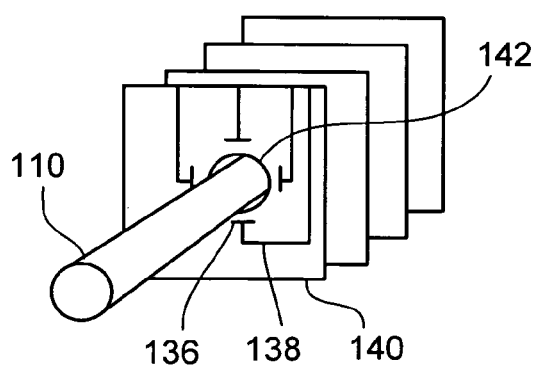
FIGS. 14 and 15 are a perspective view and a side view of a capillary and electrodes.
Figure 15:
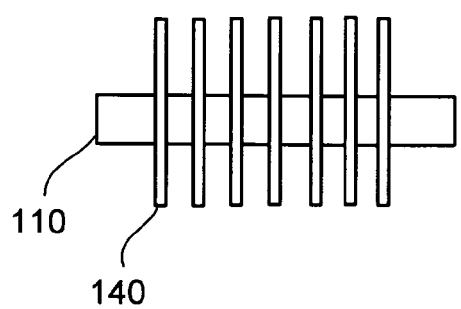

As shown in FIGS. 14 and 15, in some implementations, the electrodes 136 and electrical connections 138 may be integrated on a printed circuit board 140 (PCB) to reduce the cost of the disposable cartridge. A rigid PCB can have ten circuit layers, for example, and be ⅛" thick. A through hole 142 in the PCB would allow a capillary chamber 110 to pass through and an electrode pattern would be generated in each layer of the PCB. Multiple PCBs can be stacked to create a sample chamber of a selected length. Fluidic and electrical interconnects could be as described above. In this example, the disposable cartridge could be the capillary and the fluidic interconnects to the capillary.

Figure 17:
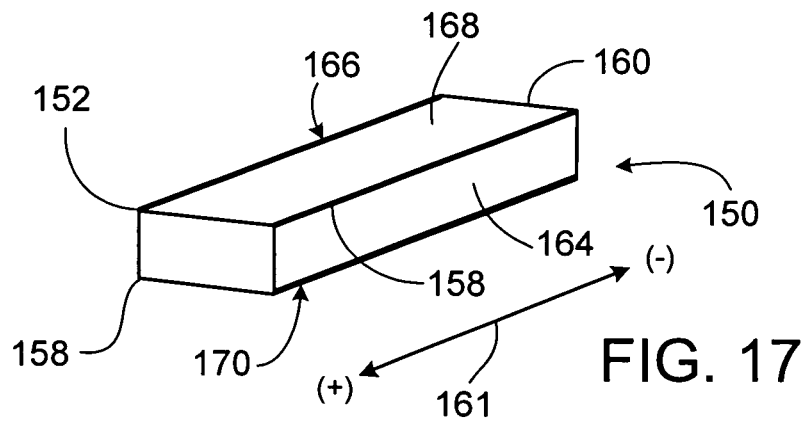
FIG. 17 is a perspective view of a disposable chamber.
Figure 18:
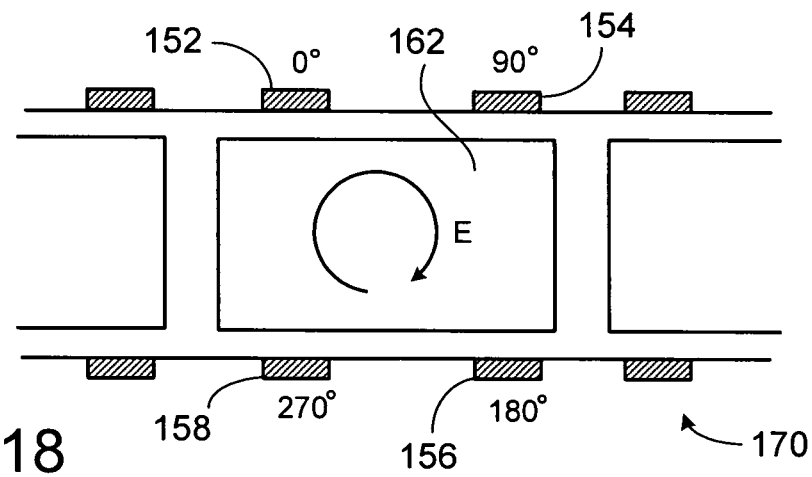
FIGS. 18 and 19 are a schematic sectional end view and a sectional top view of a set of chambers.
Figure 19:
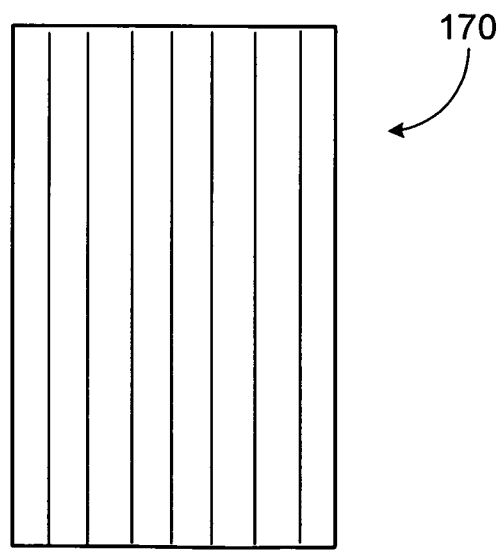

As shown in FIGS. 17 and 18, in a more comprehensive integration approach, microfluidic separation devices 150 could be fabricated in glass, quartz, polymers, epoxy, or elastomers, for example. Electrodes 152, 154, 156, 158 would be deposited at or near the corners of each channel 160 to impose a rotational electric field E to achieve longitudinal separation 161 along the length of the chamber. The electrodes may be in contact with or insulated from the medium (fluid) that is held in the sample chamber. In some implementations, the channel cross-section is square as shown in FIG. 17. The side walls 164, 166 of the sample chamber may be of the same or different material as the top or bottom substrate 168, 170. The top and bottom substrates 168, 170 may be the same or different materials. As shown in FIGS. 18 and 19, an array 170 of such sample chambers with electrodes may be fabricated using lithography, LIGA (x-ray lithography), molding, stamping, and/or printing methods. The interconnected sample chambers may define a straight or serpentine (as in FIG. 19) or any other path. The sample chamber may be a single channel or may have one or more T- or Y-junctions. A series of these channels and junctions on a device operated using a transverse propeller effect can iteratively separate enantiomers with high purity.

Figure 24:
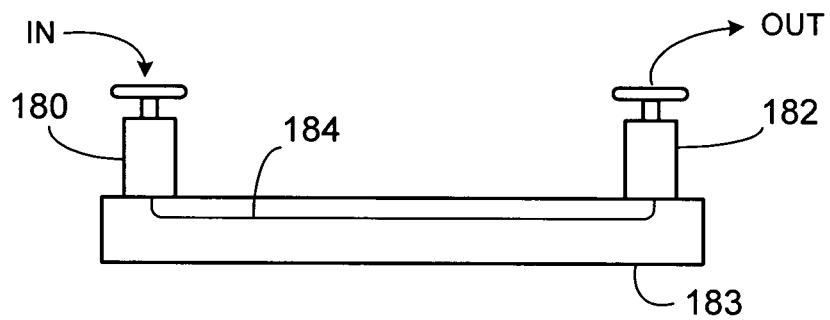
FIGS. 24 and 25 are a side view and a top view of fluidic interconnections to a chamber.

As shown in FIG. 24, fluidic connections 180, 182 to the chamber 184 may include tubing ports such as Upchurch Nanoports. A plastic housing 183 can be attached to the microchannel device to provide molded fittings to attach tubing.

Figure 25:
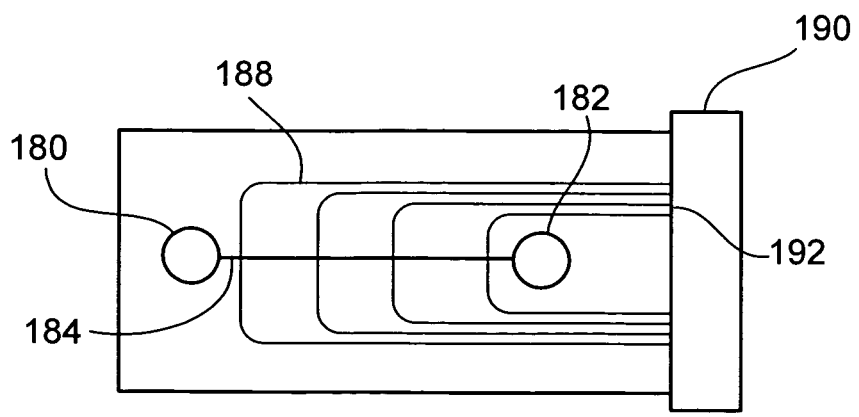

As shown in FIG. 25, electrical connections can be end-connectors, elastomeric connectors, pogo pins, or other devices 190 to make contact with the contact pads 192 of the patterned electrodes. Both fluidic (and electrical) connections may be made using a clamshell device that mechanically forms a seal around the fluidic ports and makes good contact with the bond pads. The disposable in such cases could be the microchannel device without the clamshell.

The separation techniques described here have an extremely broad range of possible applications.

In some applications, the system can determine the absolute configuration of a molecule by measuring the direction in which the molecule moves in response to the applied electric field. In such applications, the mixture may be non-pure or it may be enantiopure.

The rotation of the electric field may be reversed (using software or hardware), to confirm the absolute configuration determination, because, when the electric field is reversed, the chiral molecules of interest should travel in the opposite direction.

The separation techniques described here (which we sometimes refer to broadly as simply "the technique") may be used as a stand-alone separation system or as an add-on to another chiral separation technique (e.g., high-performance liquid chromatography, HPLC). For example, the electric field may be applied to a chiral HPLC column (for additional enrichment).

The technique may be used as an add-on to a standard HPLC column (to achieve separation of size and chirality in one step).

The technique or the resulting separations may be used for the detection, determination of composition, quantification, separation and/or purification of various objects in various fields (e.g., analytical chemistry, drug discovery, drug development, drug manufacturing, genomics, proteomics and/or glycomics) For example, the technique or the resulting separations can be applied to sugars in glycomics applications or to peptides or proteins in proteomics applications. The technique can also be applied to the purification of modified carbohydrates or protein-carbohydrate interactions. The techniques may also be used for diagnostic applications, e.g., detection and/or quantification of various post-translational modifications (e.g., glycosylation, phosphorylation) on proteins/peptides, or similar modifications on DNA (e.g., methylation) and other epi-genetic applications, or of biomarkers in disease states. The technique or the resulting separations may also be used in chemical manufacturing applications, e.g., custom synthesis, batch enrichment, in fine chemical or synthetic intermediate manufacture, or applied to agrichemicals, petrochemicals, flavors and fragrances, or used in food processing, forensic applications, and/or in academic research.

The technique or the resulting separations may also be used for the detection, determination of composition, quantification, separation, and/or removal of chiral impurities from solvents or solutions.

The technique or the resulting separations may also be used in asymmetric synthesis. Currently in asymmetric synthesis and methodology development, reactions are run sequentially or in parallel, with each reaction having different parameters (e.g., reaction conditions, catalysts) to determine the optimized reaction conditions to achieve high enantiopurity and/or a desired single enantiomer of a particular absolute (e.g., left- or right-handed) configuration. Upon completion of the chemical reaction, the reaction is worked up, purified of achiral impurities and starting materials and then, e.g., injected onto a chiral chromatography column for enantiomeric excess ratio (% ee) analysis and/or separation into pure optical isomers. The determination of the most suitable chiral chromatography column and condition choices can require significant development time. This is eventually followed by very low throughput analysis (e.g., x-ray crystallography) to determine the absolute configuration of the enantiomers. Overall, this process is laborious and time intensive, significantly adding to, for example, the development time for new asymmetric synthetic routes (e.g., in process chemistry) or for asymmetric synthesis methodology development (e.g., analysis of exploratory reactions utilizing novel chiral catalysts).

The techniques described here use a separation/analysis chamber into which a chemical reaction mixture can be directly injected without prior processing or refinement. At a given time, the reaction mixture can be transferred from a reaction vessel into the separation chamber using standard fluidic technology. A field can then be applied across the chamber that is rotating relative to the chamber to cause chiral objects present in the reaction mixture to rotate and the rotation of the objects causing them to move in a direction based on their chirality. Any achiral materials present would not move. The chiral product(s) would move at different speeds and/or directions inside of the separation chamber, allowing simultaneous: A) isolation/purification of optical isomers both from each other as well as from achiral impurities; B) determination of % ee of the reaction mixture, e.g., by comparing the area under the curve (AUC) of the separated peaks as measured by a detector; and/or C) determination of the absolute configuration of the objects based upon the direction/manner of an optical isomer's movement in the separation chamber. The reactions and analyses could be run in parallel if desired.

Similarly, at a given time, a reaction mixture from a chemical reaction that is believed or known to produce a racemic mixture of products can be transferred from a reaction vessel into the separation chamber using standard fluidic technology. When the rotating field is applied across the chamber, achiral materials would not move. The chiral product(s) would move at different speeds and/or directions allowing the processing described above. The reactions and analyses could be run in parallel if desired.

The objects may be achiral objects with chiral labels attached.

The technique can be applied to known molecules or to previously unknown molecules or to known molecules that have unknown properties as they relate to the separation techniques described here.

For molecules that are known, the system can be modeled a priori to predict, adjust, and/or optimize performance, or to detect their presence or absence in the solution.

For molecules that are unknown or have properties that are unknown, the system can be used for post-analysis, to detect, identify, and/or quantify the composition and/or the specific characteristics of the chiral objects.

The analysis may include determining the absolute configuration of a molecule, the molecule's absence or presence in the mixture, the molecule's propeller efficiency, the number of its stereocenters and their contributions to the molecule's propeller properties, or the quantitative measurement of the mixture's enantiomeric excess. The chirality of a sample may be quantified, e.g., by applying a force for translational motion in a time-gated mode, and then measuring the drag force acting on the molecule for or against the linear motion.

The formed gradient may be measured to deduce characteristics of a chiral object's electric dipole moment, its propeller properties, and/or its interaction with the solvent or with other molecules.

The technique and/or a similar setup may be used for electrorotary chemistry (e.g., chemistry, in the presence of and/or due to, a rotating electric field), e.g., chiral synthesis, catalysis and other catalytic reactions and applications, shifting of a reaction's equilibrium by separating and/or transporting the intermediate or product of the reaction, or manipulating the reaction probability of specific reactants by matching their rotations.

The technique and/or a similar setup may also be used in electrorotary chemistry to study molecular interactions, or to detect specific molecules and/or their reactions (e.g., by attaching a propeller object to single molecule and then study its properties during a reaction).

The system and the technique may be used to separate, sort, transport, purify, and/or manipulate chiral molecules and objects.

Furthermore, certain chemical reactions involving chiral molecules may be manipulated (e.g., by changing the concentration of a chiral molecule in a certain region). Or a continuous concentration gradient may be used to apply different concentrations of molecules onto an array (e.g., of surface receptors) in parallel and obtain multiple results simultaneously (rather than having to run an experiment with a different concentration of the chiral molecule each time).

In some applications, the method can be used to separate and/or purify chiral molecules from achiral impurities, using the propeller effect to remove chiral molecule(s) of interest from an initial mixture containing contaminants.

A similar approach or technique may be applied to other molecules or objects besides enantiomers, whether chiral or achiral (in which case chiral labels may be attached to make them chiral), e.g., DNA, RNA, proteins, protein post-translational modifications (PTMs), peptides, lipids, amino acids, virus, bacteria, or cells. These chiral labels may be molecules or objects that are self-assembled, self-activated, or pre-activated.

Multiple chiral labels having different, discrete propeller efficiencies may be used for multiplex assays.

Chiral labels can used for debulking and enriching sample matrices for cells and molecules of interest.

Propeller molecules can be conjugated to antibodies or to nucleic acids to provide analyte selectivity. Additional specificity can be imparted by a propeller sandwich configuration whereby two binding events must occur before a functional propeller is formed. For example, achiral conjugates can target discrete epitopes on a ligand. Presence of target molecules results in binding of both achiral conjugates in proximity, which produces a chiral propeller.

Aptamer structures can be designed as target-activated chiral labels. The unbound aptamer can be achiral or chiral and becomes chiral or oppositely chiral, respectively, in the presence of target molecules.

The propeller effect may also be induced in biomolecules without the need for chiral labels. Intermolecular interactions (antibody-antigen, protein-protein, protein-nucleic acid) can induce conformational changes. Some of these changes may change apparent propeller efficiency of the complex and can be exploited. Physicochemical conditions can be adjusted to enhance the effect between bound and unbound target molecules. For example, high pressure can reduce molecular fluctuations and rigidify the complex.

The technique will enable discovery of therapeutic compositions, in a variety of ways. Some examples are set forth below.

Skelaxin™ (Metaxalone, (±)-5-[(3,5-dimethylphenoxy) methyl]oxazolidin-2-one, CAS Registry Number=[1665-48-1]) (Appendix B) has been previously isolated and identified as a racemic mixture of its two enantiomers. The method/apparatus described here could separate the previously known racemic mixture (Metaxalone) into its purified stereoisomeric constituents which will have distinct biological and/or toxicological attributes, and to an enantiomer with properties that are preferred for therapeutic usage. An "active agent" that incorporates the preferred enantiomer of Metaxalone, when administered to a patient, alone or in combination with another compound, element, or mixture, would confer, directly or indirectly, a desired physiological effect on the patient. The indirect physiological effect may occur through a metabolite or other indirect mechanism. When the active agent is a compound, then salts, solvates (including hydrates) of the free compound or salt, crystalline forms, non-crystalline forms, and any polymorphs of the compound are included. All forms are contemplated regardless of the methods used to obtain them. All forms (for example solvates, optical isomers, enantiomeric forms, polymorphs, free compound and salts of an active agent) of the preferred stereoisomer of metaxalone or other active agent may be employed either alone or in combination.

In addition to purification and isolation of the unknown optically pure enantiomers of Metaxalone, the described technique can be used to purify or isolate other known, optically active molecules.

The technique separates stereoisomeric mixtures of biologically active substances into their purified stereoisomeric constituents, which will have distinct biological and/or toxicological attributes, enabling one purified stereoisomer to be designated as "preferred" for therapeutic usage. An "active agent" that incorporates this preferred stereoisomer for therapeutic usage, when administered to a patient, alone or in combination with another compound, element, or mixture, may confer, directly or indirectly, a desired physiological effect on the patient. The indirect physiological effect may occur through a metabolite or other indirect mechanism. When the active agent is a compound, then salts, solvates (including hydrates) of the free compound or salt, crystalline forms, non-crystalline forms, and any polymorphs of the compound are included. All forms are contemplated regardless of the methods used to obtain them. All forms (for example solvates, polymorphs, free compound and salts of an active agent) of the purified preferred stereoisomer of the biologically active substance may be employed either alone or in combination.

The technique can be used in the purification of chiral chemical intermediates in addition to the purification of chiral biologically-active substances. Examples of chiral substances that can be purified into their optically pure form by a process employing the described method/apparatus are contained in the books "Chiral Drugs", Cynthia A. Challener ed., Ashgate Publishing Ltd., 2001, and references cited there, and "Chiral Intermediates", Cynthia A. Challener ed., Ashgate Publishing Ltd., 2001, and references cited there. Additional known chiral substances that can be purified into their optically pure form by a process employing the described method/apparatus are described in the books "Chirality in Drug Research", Eric Francotte and Wolfgang Lindner eds., Wiley-VCH, 2007 and references cited there, "Fine Chemicals", Peter Polak, Wiley, 2007 and references cited there, and "The Merck Index (14$^{th}$ edition)", Merck Research Laboratories, 2006, and references cited there. All of the cited books and the references cited in them are incorporated by reference here.

Additional example chiral molecules that can be purified into their optically pure form by the technique are listed in Tables 1 and 2 (Appendix D). The five above cited references, Table 1, Table 2, and chiral molecule examples contained there are offered by way of illustration but are not meant to limit the scope of the molecules that may be subjected to the technique, both in terms of known and unknown chiral molecules that can be purified into optically pure form by the process employing the described technique.

Other implementations are also within the scope of the following claims.

Appendix A (Examples)

Six copper wire electrodes were arranged around a fused quartz capillary (FIG. 1). The electrodes and capillary were fixed in place by G10 high dielectric material to prevent arcing between the electrodes. The capillary (Polymicro, O.D. 665 um, I.D. 150 um) was connected to a pump (KDS-210) and an injection valve for sample introduction. The resulting enantiomer enrichment was detected by splitting the sample volume in half and running the leading and trailing fractions into a combination CD/UV detector (Jasco CD-2095).

A racemic mixture of 1,1'-bi-2-naphthol-bis(trifluoromethanesulfonate), sigma-aldrich #514292, was injected into the capillary surrounded by electrodes (200 nl @~0.5 mg/ml, cyclohexane). The sample was subjected to a rotating field at 10,000 volts peak-peak and 40 KHz for 17 hrs, at room temperature. Absorbance and CD measurements, both at 290 nm, were recorded for the leading and trailing fractions of the sample (approx. 100 nl each). Measurements (CD:Abs)–control mixture was +0.022:2.038, leading fraction was −0.004: 0.446, trailing fraction was +0.010:0.326. Post separation measurements were non-quantitative due to Taylor dispersion and sample dilution. The results indicated that separation did occur and that the expected propeller stereoisomer moved in the correct direction.

The experiment was repeated with 52-hour separation. Sample flow rate was reduced from 4 ul/min to 2 ul/min. Recorded measurements were −0.014:1.905 and +0.008:1.584 for leading and trailing fractions. Control was +0.022:2.038. The results were consistent with the first experiment.

In another experiment, custom compounds were used which had been synthesized according to methods described in Van Es, J. J. G. S. et al. Synthesis and characterization of optically active cyclic 6,6'-dinitro-1,1'-binaphthyl-2,2'-diethers (*Tetrahedron Asymmetry* 8, 1825-1831 (1997)). Racemic mixture of 2,2'-(1,3-propylenedioxy)-6,6'-dinitro-1,1'-binaphthlene (1b) and optically pure isomers of 2,2'-(1,4-butylenedioxy)-6,6'-dinitro-1,1'-binaphthlene (1a+, 1a−).

Figure 26:
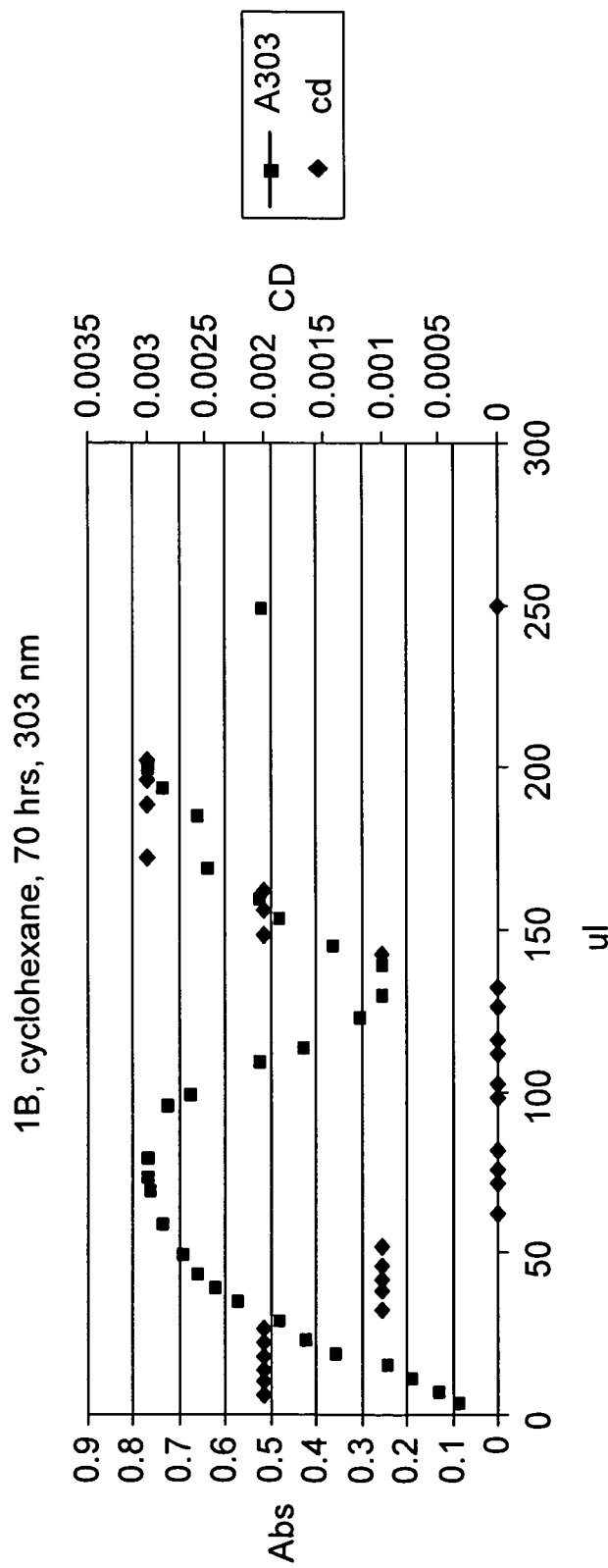
FIGS. 26 through 28 are graphs of experimental results.

In an additional experiment, compound 1b was dissolved in cyclohexane at approximately 0.5 mg/ml. Two hundred nanoliters was injected into the capillary area surrounded by electrodes and a rotating electric field was applied for 70 hrs at room temperature. Leading and trailing fractions were measured at 303 nm and compared to starting material. Results are shown in the graph in FIG. 26, which illustrated that CD values inversely correlate with absorbance during elution of the first peak and then show positive correlation during the second peak elution. The starting material had a CD value of 0.001 and absorbance of 1.577.

Figure 27:
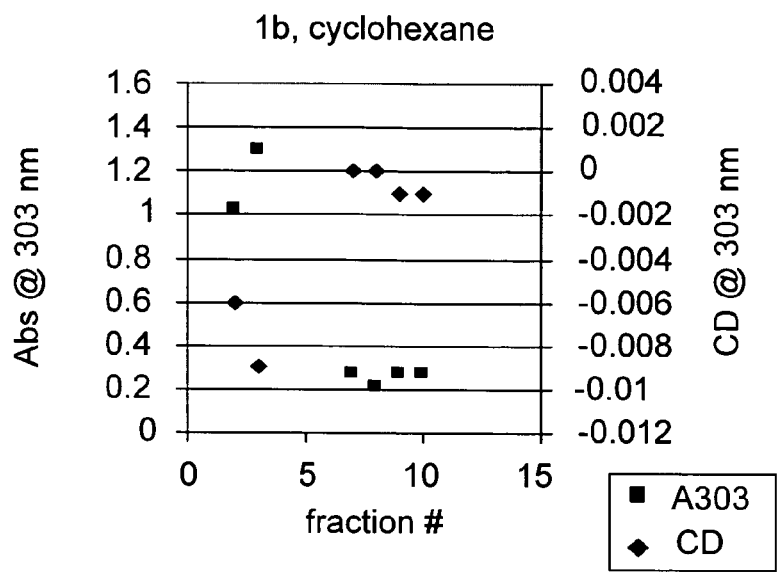

The prior experiment was repeated for 110 hrs and 250 nl fractions were collected and serially injected into the detector. The peak measurements were CD=−0.009, Abs=1.30 for the first peak (graph 2) which is consistent with results observed (FIG. 27) in the prior experiment. The second peak was not observed due to insufficient sample collection tubes.

Figure 28:
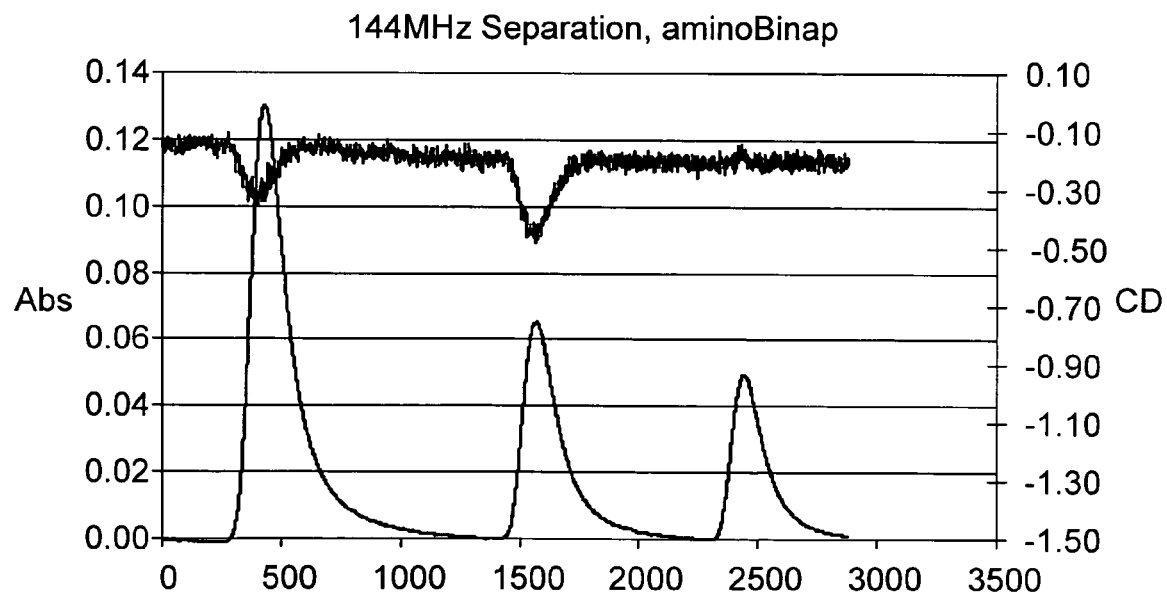

A demonstration of separation at low voltage and high frequency is shown in FIG. 28. A 10-cm long capillary (100 um ID, 360 um OD) was used as sample chamber. Four electrodes (32 g magnet wire) were fixed around the capillary using adhesive. A signal generator provided a sinusoidal signal at 1V that was passed through a 4-way splitter and amplified to 36V peak-to-peak at the sample chamber. The 90° phase shift was accomplished by adjusting the cable length from the splitter to the amplifiers (Minicircuits ZHL-03-5WF). A sample of amino binap at 0.15 mgs/ml in cyclohexane was injected into the capillary through a Rheodyne sample injector valve and introduced into the electrode region. The rotating electric field was turned on for 40 hrs and then eluted as described previously. The results show that the leading fraction (peak eluting ~1600) was enriched for the (−) enantiomer relative to the racemic starting material (peak eluting ~500). The trailing fraction (peak eluting ~2500) was enriched for the (+) enantiomer. The elution times are not meaningful because each sample was injected serially while the detector was collecting data continuously. Absorbance and CD values were monitored at 250 nm using Jasco CD-2095 detector.

The same experimental setup was repeated at 300 MHz and resulted in no enantiomeric enrichment, as expected (data not shown). This was because the electric field was rotating out of phase and not creating the propeller motion.

Appendix B (The Chiral Molecule Metaxalone)

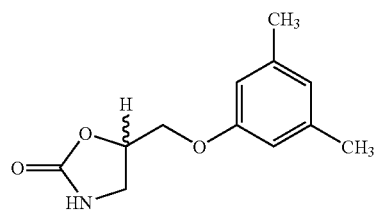 [SMILES: Cc1cc(C)cc(OCC2CNC(=O)O2)c1]

Metaxalone
(Skelaxin®, King Pharmaceuticals)
2006 US sales=$480 Million
Commercially available from chemical suppliers Appendix C (Example Chiral Molecules)

TABLE 1

| Drugs Sold Racemic (Example Trade Name) | Generic Name | Racemate CAS |
|---|---|---|
| Prevacid | Lansoprazole | 103577-45-3 |
| Effexor XR | Venlafaxine | 93413-69-5 |
| Norvasc | Amlodipine | 88150-42-9 |
| Protonix | Pantoprazole | 102625-70-7 |
| Wellbutrin XL | Bupropion | 34841-39-9 |
| Toprol XL | Metoprolol | 37350-58-6 |
| Zyrtec (3 forms in Top 200) | Cetirizine | 83881-51-0 |
| Coreg | Carvedilol | 72956-09-3 |
| Adderall XR | Amphetamine | 300-62-9 |
| Aciphex | Rabeprazole | 117976-89-3 |
| Concerta (Ritalin) | Methylphenidate | 113-45-1 |
| Aricept | Donepezil | 120014-06-4 |
| Zofran | Ondansetron | 99614-02-5 |
| Provigil | Modafinil | 68693-11-8 |
| Skelaxin | Metaxalone | 1665-48-1 |
| Allegra | Fexofenadine | 83799-24-0 |
| Ditropan XL | Oxybutynin | 5633-20-5 |
| Astelin | Azelastine | 58581-89-8 |
| Prilosec | Omeprazole | 73590-58-6 |
| Coumadin | Warfarin | 81-81-2 |

TABLE 2

| Drugs Sold Optically Pure (Example Trade Name) | Generic Name | Optically Pure CAS |
|---|---|---|
| Lipitor | Atorvastatin | 134523-00-5 |
| Nexium | Esomeprazole | 161796-78-7 |
| Singulair | Montelukast | 158966-92-8 |
| Plavix | Clopidogrel | 113665-84-2 |
| Zocor | Simvastatin | 79902-63-9 |
| Lexapro | Escitalopram | 128196-01-0 |
| Zoloft | Sertraline | 79617-96-2 |
| Topamax | Topiramate | 97240-79-4 |
| Levaquin | Levofloxacin | 100986-85-4 |
| Valtrex | Valacyclovir | 124832-27-5 |
| Zetia | Ezetimibe | 163222-33-1 |
| Cymbalta | Duloxetine | 136434-34-9 |
| Crestor | Rosuvastatin | 287714-41-4 |
| Diovan | Valsartan | 137862-53-4 |
| Nasonex | Mometasone | 105102-22-5 |
| Flomax | Tamsulosin | 106133-20-4 |
| Omnicef | Cefdinir | 91832-40-5 |

TABLE 2-continued

| Drugs Sold Optically Pure (Example Trade Name) | Generic Name | Optically Pure CAS |
|---|---|---|
| Altace | Ramipril | 87333-19-5 |
| Oxycontin | Oxycodone | 76-42-6 |
| Lyrica | Pregabalin | 148553-50-8 |
| Spiriva | Tiotropium | 186691-13-4 |
| Detrol | Tolterodine | 124937-51-5 |
| Lunesta | Eszopiclone | 138729-47-2 |
| Synthroid | Levothyroxine | 51-48-9 |
| Strattera | Atomoxetine | 83015-26-3 |
| Pravachol | Pravastatin | 81093-37-0 |
| Pulmicort | Budesonide | 51333-22-3 |
| Yasmin | Drospirenone | 67392-87-4 |
| Keppra | Levetiracetam | 102767-28-2 |
| Flovent | Fluticasone | 80474-14-2 |
| Prograf | Tacrolimus; FK-506; Fujimycin | 104987-11-3 |
| Xalatan | Latanoprost | 130209-82-4 |
| Cialis | Tadalafil | 171596-29-5 |
| Reyataz | Atazanavir | 198904-31-3 |
| Kaletra | Lopinavir | 192725-17-0 |
| Avelox | Moxifloxacin | 354812-41-2 |
| Paxil | Paroxetine | 61869-08-7 |
| Xopenex | Levalbuterol | 18559-94-9 |
| Sustiva | Efavirenz | 154598-52-4 |
| Nasacort | Triamcinolone | 124-94-7 |
| Norvir | Ritonavir | 155213-67-5 |
| Viread | Tenofovir | 147127-20-6 |
| Zyvox | Linezolid | 165800-03-3 |
| Relpax | Eletriptan | 143322-58-1 |
| Lumigan | Bimatoprost | 155206-00-1 |
| Zithromax | Azithromycin | 83905-01-5 |
| Mirapex | Pramipexole | 104632-26-0 |
| Avodart | Dutasteride | 164656-23-9 |
| Casodex | Bicalutamide | 90357-06-5 |
| Vigamox | Moxifloxacin | 354812-41-2 |
| Lescol | Fluvastatin | 93957-54-1 |
| Tussionex | Hydrocodone | 125-29-1 |
| Sensipar | Cinacalcet | 226256-56-0 |
| Inderal | Propranolol | 525-66-6 |
| Prilosec | Omeprazole | 73590-58-6 |
| Biaxin | Clarithromycin | 81103-11-9 |
| Nebcin | Tobramycin | 32986-56-4 |
| Proscar | Finasteride | 98319-26-7 |
| Kadian | Morphine | 57-27-2 |
| Codeine | Codeine | 76-57-3 |
| Travatan | Travoprost | 157283-68-6 |
| Dovonex | Calcipotriol | 112965-21-6 |
| Zomig | Zolmitriptan | 139264-17-8 |
| Suboxone | Buprenorphine | 52485-79-7 |
| Taxol | Paclitaxel | 33069-62-4 |
| Dexamethasone | Dexamethasone | 50-02-2 |

The invention claimed is:

1. A method comprising applying across a chamber a field having a field direction that rotates relative to the chamber to cause spin rotation of chiral objects in a mixture in the chamber, each chiral object's axis of rotation lying within the chiral object itself, the spin rotations of the chiral objects causing a net directional motion of the chiral objects along the axis of rotation of the field, and effecting a step of an application or process using a result of the net directional motion of the chiral objects.

2. The method of claim 1 in which the chiral objects comprise sugar molecules.

3. The method of claim 2 in which the sugar molecules comprise at least one of monosaccharides, disaccharides, oligosaccharides, or polysaccharides (glycans).

4. The method of claim 1 in which the chiral objects comprise proteins.

5. The method of claim 1 in which the chiral objects comprise peptides.

6. The method of claim 1 in which the application or process comprises a genomics application or process.

7. The method of claim 1 in which the application or process comprises a proteomics application or process.

8. The method of claim 1 also including in which the application or process comprises a glycomics application or process.

9. The method of claim 1 also including in which the application or process comprises a chemical manufacturing application or process.

10. The method of claim 1 also including in which the application or process comprises a food processing application or process.

11. The method of claim 1 also including in which the application or process comprises a forensics application or process.

12. The method of claim 1 also including in which the application or process comprises an academic research application or process.

13. The method of claim 1 also including in which the application or process comprises a solvent purification application or process.

14. The method of claim 1 also including in which the application or process comprises an asymmetric synthesis application or process.

15. The method of claim 1 in which a product outcome of a chemical reaction is purified.

16. The method of claim 1 in which a product outcome of a chemical reaction is quantified.

17. The method of claim 1 in which a product outcome of a chemical reaction is identified.

18. The method of claim 15, 16, or 17 in which a product outcome of a chemical reaction comprises a non-racemic product mixture.

19. The method of claim 15, 16, or 17 in which a product outcome of a chemical reaction comprises a racemic product mixture.

20. The method of claim 1 in which the chiral objects comprise achiral molecules that have chiral labels attached.

21. The method of claim 20 in which the achiral molecules comprise lipids.

* * * * *